US010984890B2

(12) United States Patent
Vaske et al.

(10) Patent No.: US 10,984,890 B2
(45) Date of Patent: Apr. 20, 2021

(54) SYNTHETIC WGS BIOINFORMATICS VALIDATION

(71) Applicant: Nantomics, LLC, Culver City, CA (US)

(72) Inventors: Charles Joseph Vaske, Santa Cruz, CA (US); Rahul Parulkar, Culver City, CA (US); John Zachary Sanborn, Santa Cruz, CA (US); Stephen Benz, Santa Cruz, CA (US); Mark Johnson, Culver City, CA (US)

(73) Assignee: NantOmics, LLC, Culver City, CA (US)

( * ) Notice: Subject to any disclaimer, the term of this patent is extended or adjusted under 35 U.S.C. 154(b) by 294 days.

(21) Appl. No.: 15/639,819

(22) Filed: Jun. 30, 2017

(65) Prior Publication Data

US 2018/0004893 A1    Jan. 4, 2018

Related U.S. Application Data

(60) Provisional application No. 62/357,282, filed on Jun. 30, 2016.

(51) Int. Cl.
*G16B 30/00* (2019.01)
*G06F 16/901* (2019.01)
*G16B 35/00* (2019.01)
*G16B 50/00* (2019.01)
*G16C 20/60* (2019.01)
*G16B 20/00* (2019.01)

(52) U.S. Cl.
CPC ........... *G16B 30/00* (2019.02); *G06F 16/901* (2019.01); *G16B 20/00* (2019.02); *G16B 35/00* (2019.02); *G16B 50/00* (2019.02); *G16C 20/60* (2019.02)

(58) Field of Classification Search
None
See application file for complete search history.

(56) References Cited

U.S. PATENT DOCUMENTS

| 9,092,401 | B2 | 7/2015 | Richards et al. |
| 9,262,719 | B2 | 2/2016 | Soon-Shiong |
| 2012/0059670 | A1 | 3/2012 | Sanborn et al. |
| 2012/0066001 | A1 | 3/2012 | Sanborn et al. |
| 2013/0073217 | A1 | 3/2013 | Dewey et al. |
| 2014/0045705 | A1 | 2/2014 | Bustamante et al. |
| 2014/0229117 | A1 | 8/2014 | Halpern et al. |
| 2014/0287934 | A1* | 9/2014 | Szelinger ............... G16B 30/00 506/2 |
| 2016/0034638 | A1 | 2/2016 | Spence et al. |

FOREIGN PATENT DOCUMENTS

| CA | 3 029 029 A1 | 1/2018 |
| CN | 109791796 A | 5/2019 |
| JP | 2006-277611 A | 10/2006 |
| JP | 2013-545439 A | 12/2013 |
| JP | 2019525308 A | 9/2019 |
| KR | 20190039693 A | 4/2019 |
| WO | 2011/139345 A2 | 11/2011 |
| WO | 2012037456 A1 | 3/2012 |
| WO | 2013/062505 A1 | 5/2013 |
| WO | 2016/062713 A1 | 4/2016 |
| WO | 2018006057 A1 | 1/2018 |

OTHER PUBLICATIONS

Pabinger et al., "A survey of tools for variant analysis of next-generation genome sequencing data", Briefings in Bioinformatics. vol. 15. No. 2. 256278, Advance Access published on Jan. 21, 2013.
Roth et al., "JointSNVMix: a probabilistic model for accurate detection of somatic mutations in normal / tumour paired next-generation sequencing data", Bioinformatics vol. 28 No. 7 2012, pp. 907-913.
Xu et al., "Comparison of somatic mutation calling methods in amplicon and whole exome sequence data", BMC Genomics 2014, 15:244, http://www.biomedcentral.com/1471-2164/15/244.
Examination report No. 1 for Patent Application No. CA3029029 dated Oct. 8, 2019, 8 pages.
Examination report No. 1 for Patent Application No. AU 2017290840, dated Jul. 29 2019.
Second Office Action received for Australian Patent Application Serial No. 2017290840 dated Mar. 16, 2020, 4 pages.
Third Office Action received for Australian Patent Application Serial No. 2017290840 dated Apr. 15, 2020, 4 pages.
Extended European Search Report received for European Patent Application Serial No. 17821417.7 dated Mar. 5, 2020, 11 pages.
Cottrell et al., "Validation of a Next-Generation Sequencing Assay for Clinical Molecular Oncology", Journal of Molecular Diagnostics, Jan. 1, 2014, vol. 16, No. 1, pp. 89-105.
Office Action received for Japanese Patent Application Serial No. 2018568675 dated Apr. 21, 2020, 10 pages (Including English Translation).
International Search Report and Written Opinion received for PCT Application Serial No. PCT/US2017/040455 dated Sep. 20, 2017, 10 pages.
International Preliminary Report on Patentability received for PCT Application Serial No. PCT/US2017/040455 dated Jan. 10, 2019, 8 pages.
International Search Report Written Opinion received for Singaporean Patent Application Serial No. 11201811286S, dated Apr. 16, 2020, 8 pages.
Yuan et al., "Read-mapping using personalized diploid reference genome for RNA sequencing data reduced bias for detecting allele-specific expression", IEEE Int Conf Bioinform Biomed Workshops, 2012, pp. 718-724.

(Continued)

*Primary Examiner* — John S Brusca
(74) *Attorney, Agent, or Firm* — Martin Fessenmaier; Umberg Zipser LLP

(57) ABSTRACT

Systems, methods, and devices for generating synthetic genomic datasets and validating bioinformatic pipelines for genomic analysis are disclosed. In preferred embodiments, synthetic maternal and paternal datasets with known variants are used with matched normal synthetic datasets to validate various bioinformatic pipelines. Bioinformatic pipelines are evaluated using the synthetic datasets to assess design changes and improvements. Accuracy, PPV, specificity, sensitivity, reproducibility, and limit of detection of the pipelines in calling variants in synthetic datasets is reported.

18 Claims, No Drawings

(56) References Cited

OTHER PUBLICATIONS

Zook et al., "Integrating human sequence data sets provides a resource of benchmark SNP and indel genotype", Nat Biotechnol, Feb. 16, 2014, 32, pp. 246-251.
Office Action received for Canadian Patent Application Serial No. CA3029029 dated Jun. 18, 2020, 4 pages.
Decision of Refusal received for Japanese Patent Application Serial No. 2018568675 dated Nov. 17, 2020, 2 pages (Including English Translation).

* cited by examiner

SYNTHETIC WGS BIOINFORMATICS VALIDATION

This application claims priority to U.S. provisional application Ser. No. 62/357,282, filed Jun. 30, 2016, incorporated by reference herein.

FIELD OF THE INVENTION

The field of the invention is validation systems and methods for detection of genetic variation, especially as it relates to computational analysis of whole genome data.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

With the advent of whole genome sequencing (WGS) and next generation sequencing platforms, massive quantities of data are now available for analysis. While the wealth of data is certainly desirable from a clinical perspective, various difficulties have arisen. For example, in most clinical whole genome analyses, it is not uncommon to oversample tumor tissue between 30-100 fold while oversampling matched normal tissue at least 10-30 fold, where most of the genetic information is obtained from sequencing machines in fragments having a size around 100-400 bases. As such, significant computing power is needed to accurately reassemble a genome and identify a change in the genome.

For example, a recent article (BMC Genomics 2014, 15:244) compared various somatic mutation callers using BAM files as input, including MuTect, GATK UnifiedGenotyper with simple subtraction, SomaticSniper, Strelka, and VarScan2. Here, NIST-GIAB (variant set for reference individual NA12878 by the NIST-led "Genome in a Bottle" Consortium) was used as standard for evaluation. Not surprisingly, the sensitivity of some algorithms was higher than that of others using the same standard. While providing some guidance, such analysis will however not allow taking into account variations in the sample, or identification of detection limits as a fixed input set is provided. Further, each algorithm is designed with underlying assumptions that can impact the efficacy of the analysis computing platform.

More recently, BAMBAM was developed (see US20120059670 and US20120066001) that enables detection of changes between tumor and matched normal using incremental and synchronous location guided alignment. Advantageously, such system and method allows for detection of allele specific changes, and enables detection and characterization of small scale (e.g., SNP) to large scale (e.g., intrachromosomal and interchromosomal rearrangements) events. Still further, the statistical base calling approach in BAMBAM allows to accommodate for allele variants as well as artifacts and low-quality reads that are not uncommon in high throughput sequencing. While at least theoretically statistical approaches can be optimized in sequence analysis algorithms, there are no known systems and methods to evaluate changes in or validate existing analysis computing devices that leverage various computer implemented algorithms or new algorithms.

Thus, there remains a need for systems and methods to evaluate or validate performance of a specific genetic analysis tool, especially where analysis is genomic analysis.

SUMMARY OF THE INVENTION

The inventive subject matter is directed to various systems and methods to validate or calibrate genomic analysis computing devices and their implementations of genomic analysis algorithms to ensure quality and accuracy of mutation calling in such algorithms. Most preferably, contemplated systems and methods use a first plurality of virtual genomes having defined mutations simulating a tumor tissue genome and a second plurality of virtual genomes simulating a matched normal tissue genome. It should be noted that the digital virtual genomes may be prepared in numerous formats, and especially preferred formats include BAM files representing the entire genome (or one or more chromosomes or portions thereof) and files representing simulated reads generated from the virtual genomes.

In particularly preferred aspects, the preparation of the virtual genomes will start from a known human reference genome (e.g., human reference genome rg19 from USCS browser) that is then modified using SNP variations, and insertions, deletions, and copy number variations, each of which may vary in size and position. The so generated synthetic or simulated data set is then used to evaluate performance and/or validate function of a genomic analysis algorithm.

Various objects, features, aspects and advantages of the inventive subject matter will become more apparent from the following detailed description of preferred embodiments.

DETAILED DESCRIPTION

The inventive subject matter is directed to construction and use of synthetic digital patient data sets that can be used to evaluate changes in a computer implemented genomic analysis algorithm and to test/validate the performance of a genomic analysis computing device with respect to algorithm implementations in accurately calling alterations in a patient's genome. Most preferably, contemplated systems and methods use a plurality of synthetic patient genomes for male and female patients in which each of the synthetic patient genomes is based on a single reference genome, and in which each of the synthetic patient genomes has known and different genomic alterations (e.g., SNP, indels, copy number changes) to so simulate data set of a tumor tissue sample. Moreover, it should be appreciated that each simulated data set of the tumor tissue has a corresponding matched normal synthetic patient genome to so simulate a data set of a matched normal (non-diseased) tissue sample. In some embodiments, the reference genome without inserted variants (e.g., SNP, SNV, indel, etc) is used as the matched normal synthetic genome. However, it is also contemplated that other synthetic patient genomes can be used as the matched normal set (e.g., paternal/maternal combinations with additional variants, reference genomes from databases, hg19, etc) as appropriate to so allow for genomic analysis (e.g., BAM BAM, etc)

In still further contemplated aspects, performance and validation of the genomic analysis algorithms is tested with more than one, and most typically with at least 10 different tumor and matched normal synthetic patient genomes. Additionally, it is contemplated that the plurality of synthetic patient genomes for male and female patients may be present in various formats, and especially preferred formats include BAM, VCF, FASTA, FASTQ, GAR, and RAW formats.

In general, and as noted above, the inventors have constructed synthetic datasets that can be used as calibration tools to demonstrate both the limit of detection ("LoD") and repeatability of the various classes of variants detected by genomic analysis algorithms, and in some cases the accuracy, sensitivity, and specificity of detection. Typically genomic analysis algorithms input a tumor sample (whole genome sequence) at a depth of 50× coverage and a matched normal sample (whole genome sequence) at a depth of 25× coverage. Of course, it should be appreciated that alternative sequencing depths for tumor and matched normal are also deemed suitable and include 1-10×, 10-20×, 20-50×, 50-100×, 100-200×, and even higher. Most typically, the data sets will simulate male and female patients and also include matched normal data.

To maximize accuracy of variant calling, all input data are used simultaneously in the statistical models to call variants. Most typically, and depending on the particular algorithm tested, the reported variants include: (a) somatic single nucleotide variants (SNVs) that are specific to the tumor sample and are typically deemed to have arisen in the tumor; (b) germline SNVs that are present in both the tumor and normal DNA; (c) somatic indels representing insertions and/or deletions of a small size, typically fewer than a dozen bases; (d) germline indels representing insertions or deletions of a small size, typically fewer than a dozen bases; and (e) somatic copy number amplifications. It should be appreciated that variants specific to the tumor sample are considered to have arisen in the tumor, and are referred to as somatic since they are unlikely to affect the germline. Further, germline SNVs are expected to be present in both the tumor and normal DNA.

The outputs of the genomic analysis algorithms can then be evaluated on the synthetic patient data with every change to the algorithm, and a report summarizing these results will be generated. This report will give the accuracy and level of detection for the above variants, preferably using a panel of a plurality (e.g., 10, or 20, or 30 or more) synthetic patient data at the limit of detection of the current clinical assay, which is 25% cellular purity. Of course, cellular purity can also be higher (e.g., between 30-40%, or between 40-50%, or even higher) or lower (e.g., between 5-15%, or between 15-25%). Also, to assess reproducibility of the algorithm, at least one of the synthetic patient data can be run repeatedly (e.g., at least 10 times, or at least 15 times, or at least 20 times) at 100% tumor purity, and additionally at substantially lower purities (e.g., 5%, 10%, 15%, 25%, and 50%), to establish a lower limit of detection for the in silico-generated synthetic patient data.

With respect to the synthetic patient datasets it is contemplated that multiple data sets are prepared to simulate a plurality of patients. Most typically, contemplated systems and methods will include data sets corresponding to at least 5 distinct patients, or at least 10 distinct patients, or at least 20 distinct patients. Moreover, it should be appreciated that each simulated patient dataset will comprise a somatic (tumor) data set and a matched normal (germline) data set. In less preferred aspects, however, the matched normal data set may be a single synthetic data set for a plurality of patients, or even a data set for a known reference genome. In preferred aspects, however, the matched normal data set may include a synthetic 'matched normal' genome sequence, modifications relative to a reference genome sequence (e.g., hg19 from UCSC browser) that formed the basis of the synthetic 'matched normal' genome sequence, and simulated FASTQ reads of the synthetic genome sequence. Similarly, the tumor data set may include a synthetic 'tumor genome' sequence, modifications relative to the synthetic 'matched normal' genome sequence that formed the basis of the synthetic 'tumor genome' sequence, and simulated FASTQ reads of the synthetic 'tumor genome' sequence. In cases where modifications of genomic sequences are random, a random number generator will be started from a known seed for that synthetic genome sequence. It should be appreciated that using such data sets will allow not only testing and validation of accuracy, sensitivity, specificity, and reproducibility of variant calling by genome analysis algorithms (using the synthetic 'tumor genome' and 'matched normal' sequences), but also testing and validation of all computing components involved in grouping, transport, annotation, and indexing of the simulated reads (using the simulated FASTQ reads of the synthetic genome sequence). It should be appreciated that the disclosed system provides a deterministic foundation from which an entire genomic analysis system can be validated or optimized.

Moreover, once genome analysis algorithms have produced respective output files, performance of downstream components can be validated or evaluated using the respective output files as input parameters. For example, contemplated downstream components include pathway analysis engines to identify druggable targets such as PARADIGM as described in WO 2011/139345 and WO 2013/062505, or medical reasoning engines to identify clinical trials for which a patient may qualify as disclosed in U.S. Pat. No. 9,262,719. Therefore, it should be appreciated that contemplated systems and methods may be employed in the testing and validation of an entire genomic analysis ecosystem from generation of sequence reads at the sequencing machine level to transport, annotation, indexing, and variant calling, and ultimately to clinical analysis engines that consume output data provided by genome analysis algorithms.

Construction of Synthetic DNA Datasets

For example, a simulated patient's synthetic matched normal sequence may be derived from a known reference genome, and it should be appreciated that all reference genomes are deemed suitable for use herein. However, especially preferred reference genes are human reference genomes, which may or may not be further biased using a specifying factor such as race, ethnicity, family background, geographic location, predisposition to or diagnosis with a disease, etc. For example, the human hg19 or hg38 from UCSC may be employed as reference sequence, or GRCh38 from the Genome Reference Consortium. Most typically, SNP variants are first randomly generated, saved, and then used to modify the reference genome to create a maternal reference and a paternal reference (i.e., a diploid genome).

In some embodiments, the nature of the synthetic data set is described using metadata, possibly stored in one or more separate digital files. The metadata includes the various values and data structures that permit others to reproduce the validation process. Example metadata can including one or more of the following: a random seed used to generate the synthetic data, name and version number of random number sources or generators, name and version numbers of algorithms to be validated, name and version numbers of mutation sources or generators, listing of all mutations (e.g., SNP, indels, etc.) generated and their locations, name and version number of base-line genome, or other factors. It should be appreciated that providing the metadata, including the seed(s) used for random number generators, allows third parties to exactly reproduce the validation results via a deterministic random number generation. Such an approach is considered advantageous especially when validation results are leveraged for certification of the systems, for publication, or for optimization of the genomic analysis computing platform.

With respect to SNP sampling it is contemplated that tumor-normal genotyping analysis from whole genome sequencing typically results in ~1e6 homozygous, non-reference sites, and ~7e5 heterozygous, non-reference sites. To approximately match this observed variation, the inventors randomly selected a subset of sites from the dbSNP database with observed population frequencies. First, sites with a majority allele frequency >80% are filtered out to increase the chances of sampling heterozygous sites. Then, each dbSNP site is considered iteratively. With a 40% chance, that site is ignored. With a 9% chance, the site is sampled as homozygous from the population allele frequencies. With a 51% chance, two different alleles are sampled from the population frequencies, with replacement. This mixture results in approximately 1e6 non-reference homozygous sites, and 7e5 heterozygous non-reference sites. Heterozygous sites are assigned to maternal or paternal haploid genomes randomly.

Using the dbSNP variants created in the previous step, a maternal genome is created by modifying chromosomes 1-22 and chromosome X with the dbSNP variants generated above and outputting a FASTA sequence. A paternal genome is created by modifying chromosomes 1-22, and then one of chromosome X or Y with a 50% probability based on the normal seed. These two FASTA files are then combined into a single FASTA sequence with maternal chromosomes having a suffix of \_m on the name, and paternal chromosomes having a suffix of \_f.

To generate simulated read files that would produce the synthetic matched normal genome, a FASTQ dataset (e.g., 5×, 10×, 15×, 20×, 25×, 30×, 35×, 40×, more than 50×, but preferably 25×) is created by sampling simulated reads (e.g., 50 bp, 75 bp, 100 bp, 150 bp, 200 bp, 250 bp, or more, but preferably 150 bp) with SimSeq to the appropriate depth, using a read error and base quality profile generated from sequencing data from the sequencing lab from a sample (e.g., frozen sample, FFPE, laser microdissection, etc). The coverage level (preferably 25×) is simulated to hit the lowest acceptable coverage to be generated by the lab. The percentage of duplicate reads is 10%, meaning that the total coverage with duplicate reads is approximately 27.8×.

The simulated synthetic tumor genome sequence can be generated from modification of the corresponding simulated patient's synthetic matched normal genome. Most typically, the modifications will include SNVs, indels, and copy number variations, and other known tumor associated genetic changes. Of course, it should be appreciated that some or all of these changes can be based on known variations occurring in cancer, or may be entirely randomly generated.

For example, somatic SNVs may be effected as follows: For the maternal and paternal haploid genomes, single base changes are generated at random locations through the genome. For each haploid genome SNVs can be drawn from three sources: 1) COSMIC mutations, 2) somatic TCGA mutations, and 3) random locations in the genome. In one exemplary approach, approximately 500 mutations are selected from COSMIC, and 2000 from TCGA, such that a choice is rejected and retried if it is within 300 bp of a previous mutation. Finally, a random number between 2,500 and 25,000, and that number of random sites within the genome are mutated. These relative sizes were chosen to simulate a typical number of SNV in the coding regions of genes, and to also allow evaluation of mutations in intronic and intergenic regions. The site selection is performed independently between the maternal and paternal genomes, meaning that any up to two mutations may be within 300 bp of each other when the two haploid genomes' mutations are combined. However, numerous alternative methods may also be employed and may be guided by grafting actual tumor sequence information from a single or multiple patients into the genome, or by random generation of SNV.

With respect to somatic indel generation it is contemplated that in both the maternal and paternal genomes, 250 small deletions are created, of a random length uniformly between 1 and 10 bp. Similarly, in both the maternal and paternal genomes, 250 small insertions are created, of a random length, uniformly between 1 and 10 bp. Most typically, the sites for these indels are chosen to be 300 bp away from any existing SNV or indel variant, within an exonic region. It is contemplated while this may result in far more exonic indels than in typical samples, it will allow better evaluation of indel caller performance of genomic analysis algorithms. Of course, it should be appreciated that the size and number of the small indels may vary, and suitable numbers of indels may be between 20-50, between 50-100, between 100-250, between 250-500, between 500 and 1,000, and even more. Likewise, the length may be between 1-10, 10-20, 20-50, 50-100, and even longer.

Likewise, somatic copy number generation may be effected as follows. For each of the paternal and maternal haploid genomes non-overlapping copy number modifications can be generated. Events are typically generated separately for each haploid genome. The following events are randomly chosen in the chromosome: (i) 25 small deletions, each with a size randomly chosen from 5,000 bp to 500,000 bp; (ii) 25 small tandem amplifications, each with a size randomly chosen between 5,000 bp to 500,000 bp. These amplifications have copy number between 2 and 5, randomly chosen; (iii) 10 small tandem hyperamplifications, with size 5,000 to 500,000 bp, and copy number randomly chosen between 15 and 30; (iv) Large arm/chromosome deletions, each with a size between 30% and 100% of a chromosome, anchored to a telomere. The number of "arm" deletions is drawn from a Poisson distribution with mean 1; (v) Large arm/chromosome tandem amplifications, each with a size between 30% and 100% of a chromosome, anchored to a telomere. The number of "arm" deletion events is drawn from a Poisson distribution with mean 3. The number of tandem duplications is 2 plus a draw from a Poisson distribution with mean 1.0. A final tumor reference genome is generated by applying the copy number changes to the tumor haploid genomes modified by the small polymorphisms. As before, the above parameters are merely provided to give exemplary guidance, but actual numbers may vary, depending on the particular type of tumor model to be generated.

Simulated tumor DNA read data are preferably generated in FASTQ format by sampling a dataset (e.g., 5×, 10×, 20×, 30×, 40×, 50×, 70×, 100×, but preferably 50×) with SimSeq, with X % of the reads coming from the final tumor reference diploid genome, and (100−X) % of the reads from the germline diploid genome, where X is the molecular tumor percentage. This X is chosen based on the desired cellular purity (e.g. 10%, 20%, 25%, 35%, 40%, 50%, and 100% cellular purities) and differs from the cellular purity that would be estimated from a pathological slide, due to differences in the tumor genome ploidy, as the tumor genome contributes a differing amount of DNA to the mixture than a normal human cell with ploidy of 2. This molecular purity (X), is derived from a desired cellular purity (c) and the tumor ploidy (p) via the relation: $X=p*c/(p*c+2*(1-c))$.

During the genome and read generation process, all variants used are stored for use as a gold standard for further analysis. To thoroughly assess performance at the limit of detection on a wide variety of genomes, 20 different synthetic patients are preferably generated as described above at, for example, 30% cellular purity, but can also be 10%-90%, 20%-80%, 30%-70%, or 40%-60% cellular purity. Each patient's random seeds will be recorded, and 25× (or 50×, 100×, 150×, 200×, 250×, or more than 250×) coverage of the normal genome and 50× (or 100×, 150×, 200×, 250×, or more than 250×) coverage of the tumor genome will be generated using these seeds. All of the small modifications as well as all of the copy number modifications are recorded as gold standards for the assessment of variant callers. Note that some variants will fall into unmappable areas of the genome due to random chance, and that these variants will be excluded from analysis. In addition, one sample will be used for limit of detection study, and will be sampled at cellular purities of 5%, 15%, 25%, 30%, 50%, and 100%. Finally, the 100% LoD sample will be run through the pipeline 10 times to assess reproducibility of the bioinformatics pipeline. Construction of RNA Datasets essentially follows the same protocol as described for DNA above.

Example 1—Synthetic WGS Bioinformatics Validation

Methods of the inventive subject matter were used to test/validate the performance of a genomic analysis computing device (bioinformatics pipeline) with respect to algorithm implementation in accurately calling variants in a patient's genome. Synthetic genomic datasets were constructed, for example, by the methods described herein. Advantageously, it is contemplated such datasets can be used to support CLIA validation of the pipeline. Inputs to the pipeline included (1) normal sample whole genome sequencing at a depth of 25× coverage. and (2) tumor sample whole genome sequencing at a depth of 50× coverage. Variants assessed include SNVs and indels, both germline and somatic, as well as somatic copy number amplifications.

Assessment of Somatic SNVs

Accuracy, Sensitivity and Specificity: Accuracy of somatic single nucleotide variants will be assessed on the nucleotide level using the 20 synthetic patients with 30% cellular tumor purity. Since somatic variants are chosen at random, possibly deterministically, throughout the genome, many of these random locations will end up in unmappable or poorly mappable regions. For each patient, each base in a RefSeq exon, preferably a coding region, will be categorized as one of the following three categories:

(i) Mappable variant: the synthetic patient has a somatic variant at the location. Additionally, in a 100% pure tumor sample, the allele fraction is >45%, and the overall read count at the site is greater than 10. Preferably, at least 20 reads in the tumor sample have a mapping quality greater than 10, and at least 10 reads in the normal sample have a mapping quality greater than 5. (ii) Unmappable variant: the synthetic patient has a variant, but it does not meet the criteria for a mappable variant. (iii) Reference site: the patient's synthetic genome is reference at this site.

Accuracy is defined as (TP+TN)/(TP+TN+FP+FN); Positive predictive value (PPV) is defined as TP/(TP+FP); Sensitivity is defined as TP/(TP+FN); and Specificity is defined as TN/(TN+FP). Assessment is then performed as shown in Table 1 below.

TABLE 1

|  | Synthetic Tumor Genome | |
| --- | --- | --- |
|  | Mappable Variant (M or F) | HG 19 Reference Site |
| Predicted variant | TP | FP |
| Incorrect or no prediction | FN | TN |
|  | Sensitivity TP/ (TP + FN) | Specificity TN/ (TN + FP) |

In preferred aspects, acceptance criteria are typically defined as follows: All datasets must show >=95% PPV, >=95% sensitivity, >=99% specificity, and >99% accuracy. Failure Criteria are Any dataset that shows <95% PPV, <95% sensitivity, <99% specificity or <99% accuracy. In the event that any of the samples fail to meet the acceptance criteria, all should be repeated.

With respect to repeatability it is contemplated that a single synthetic patient sample with 100% tumor purity will be run ten times for repeatability. For this comparison, the initial run will be used as the gold standard for each reproducibility test. Here, acceptance criteria are typically defined as follows: All datasets must show >99.99% concordance between the first and subsequent replication, and failure criteria are typically defined as follows: Any subsequent run that shows <99.99% concordance between observed versus expected. As before, in the event that any of the samples fail to meet the acceptance criteria, all should be repeated.

Limit of Detection: The limit of detection for somatic single nucleotide variants will be assessed using the repeatability sample. The tumor WGS simulated reads contains "normal infiltrate." The percentage of tumor reads will typically be run at the following levels: 5%, 10% 15%, 20%, 25%, 30%, 40%, and 50%. The limit of detection will be the lowest bin such that it and all bins of higher allele frequency have >=75% PPV, >=99% specificity, and >=95% sensitivity.

Assessment of Germline SNV Detection

With respect to accuracy, sensitivity and specificity it is contemplated that each base of the hg19 reference genome will be assessed according to the Table 2 below. A germline variant is defined to be the genotype (including heterozygosity) chosen for the normal genome during the genome generation process. Germline variants will be categorized as a mappable variant, an unmappable variant, or a reference site, as previously described. In some embodiments, a relatively low number (e.g., 10, or 20, or 30) of synthetic patients generated for the somatic SNV detection study will be used for this study.

TABLE 2

| | Final Germline Genome | | |
|---|---|---|---|
| | Germline Variant | non-N Reference Hg19 base | |
| Predicted variant | TP | FP | Precision TP/(TP + FP) |
| Incorrect or no prediction | FN | TN | Negative Predictive Value FN/(FN + TN) |
| | Sensitivity TP/ (TP + FN) | Specificity TN/ (TN + FP) | |

Positive predictive value (PPV) is defined as TP/(TP+FP) Accuracy is defined as (TP+TN)/(TP+TN+FP+FN); Sensitivity is defined as TP/(TP+FN); and Specificity is defined as TN/(TN+FP). In preferred aspects, acceptance criteria are defined as follows: All datasets must show >=95% PPV, >=95% sensitivity and >=99% specificity. Failure Criteria are defined as follows: Any dataset that shows <95% PPV, <95% sensitivity, or <99% specificity. In the event that any of the samples fail to meet the acceptance criteria, all should be repeated.

With respect to repeatability it is contemplated that the single synthetic patient sample with 100% tumor purity will be run ten times for repeatability. Acceptance criteria are defined as follows: All datasets must show >99.99% concordance between the first and subsequent replication. Failure criteria are defined as follows: Any run that shows <99.99% concordance between observed versus expected. In the event that any of the samples would fail to meet the acceptance criteria, all should be repeated.

Limit of Detection: Since germline variants are not affected by tumor purity, the limit of detection was not assessed.

Assessment of Somatic Indels

With respect to the metrics and prediction evaluation it should be recognized that the evaluation of predictions is on a base level, for each possible position where an indel could be reported, it is classified as a positive or negative. As with SNV evaluation, the gold set will be limited by those that are in mappable coding regions, using the following classification, as previously described: (i) mappable variant, (ii) unmappable variant, and (iii) reference site. It is contemplated that the evaluated indels can be of various length, such as 5, 10 15, 20, 25, 50, or 75 bp. In preferred embodiments only indels of length <=15 bp are evaluated, while indels of greater length are filtered out.

Accuracy is defined as (TP+TN)/(TP+TN+FP+FN); Positive predictive value (PPV) is defined as TP/(TP+FP); Sensitivity is defined as TP/(TP+FN); Specificity is defined as TN/(TN+FP). Calculations are as shown in Table 3 below. The simulated numbers of indels match up well with what is found in clinical samples, however the number of events typically seen in RefSeq genes is quite small. So metrics will be evaluated by pooling the results from RefSeq gene regions.

TABLE 3

| | Synthetic Tumor Genome | |
|---|---|---|
| | Mappable Variant (M or F) | HG 19 Reference Site |
| Predicted variant | TP | FP |
| Incorrect or no prediction | FN | TN |
| | Sensitivity TP/ (TP + FN) | Specificity TN/ (TN + FP) |

Accuracy will be assessed across the variability samples. Acceptance Criteria are defined as: The pooled results must show >=95% PPV, >=95% sensitivity and >=99% specificity. Failure criteria are defined as: Any dataset that shows <95% PPV, <95% sensitivity or <99% specificity.

Repeatability: A single synthetic patient sample with 100% tumor purity (e.g., used in the accuracy study) will be run ten times for repeatability. Acceptance Criteria are all datasets must show >99.99% concordance between the first and subsequent replication. Failure Criteria are any pipeline run that shows <99.99% concordance between observed versus expected. In the event that any of the samples fail to meet the acceptance criteria, all should be repeated.

Limit of detection: The limit of detection for indels will be assessed using the repeatability sample. The tumor WGS simulated reads contains "normal infiltrate." The percentage of tumor reads will be run at the following levels: 5%, 10% 15%, 20%, 25%, 30%, 40%, and 50%. The limit of detection will be the lowest bin such that it and all bins of higher allele frequency have >=75% PPV, >=99% specificity, and >=95% sensitivity.

Assessment of Germline Indels

With respect to suitable metrics and prediction evaluation it is contemplated that evaluation of predictions is on a base level, for each possible position where an indel could be reported, it is classified as a positive or negative. As with SNV evaluation, the gold set will be limited by those that are in mappable coding regions, using the following described classifications: (i) Mappable variant: the synthetic patient has a somatic variant at the location. Additionally, in a 100% pure tumor sample, the allele fraction is >45%, and the overall read count at the site is greater than 20. (ii) Unmappable variant: the synthetic patient has a variant, but it does not meet the criteria for a mappable variant. (iii) Reference site: the patient's synthetic genome is reference at this site. Calculations are performed as shown in Table 4 below.

TABLE 4

| | Synthetic Tumor Genome | |
|---|---|---|
| | Mappable Variant (M or F) | HG 19 Reference Site |
| Predicted variant | TP | FP |
| Incorrect or no prediction | FN | TN |
| | Sensitivity TP/ (TP + FN) | Specificity TN/ (TN + FP) |

Accuracy is defined as (TP+TN)/(TP+TN+FP+FN); Positive predictive value (PPV) is defined as TP/(TP+FP); Sensitivity is defined as TP/(TP+FN); Specificity is defined as TN/(TN+FP). As with somatic indels, the number of events typically seen in RefSeq genes is quite small, and metrics will be evaluated by pooling the results from RefSeq gene regions.

Accuracy will be assessed across the variability samples. Acceptance Criteria are defined as: The pooled results must show >=95% PPV, >=95% sensitivity and >=99% specificity. Failure criteria are defined as: Any dataset that shows <95% PPV, <95% sensitivity or <99% specificity.

Repeatability: The single synthetic patient sample with 100% tumor purity (used in the accuracy study) will be run ten times for repeatability. Acceptance criteria defined as: All datasets must show >99.99% concordance between the first and subsequent replication. Failure criteria defined as: Any pipeline run that shows <99.99% concordance between observed versus expected. In the event that any of the samples fail to meet the acceptance criteria, all should be repeated.

Limit of detection: Since germline variants are not affected by purity, limit of detection will not be assessed.

Assessment of Somatic Amplifications

In some embodiments, mappable regions of the genome are collected using sequencing data from one of the simulated normal genome sequences. A region can be defined as "mappable" if it at least one read maps inside of the region with a mapping quality >0. However, it is contemplated that "mappable" can require (i) 2, 5, 10, 15, 20, or 50 reads map inside the region with a mapping quality >0, (ii) one read maps inside the region with a mapping quality greater than 0, 1, 5, 10, 15, 20, or 50, or (ii) some other minimum number of reads satisfies a minimum mapping quality. The union of the mappable genomic regions for the simulated normal genome sequences from 5 simulated patients can be generated, though in some embodiments 2, 4, 10, 15, or 20 simulated patients can be used. In general, the regions of the genome not represented in this mappable union are deemed unmappable and are not reported.

Each base in the reference genome will be assessed according to Table 5 below:

TABLE 5

| | VCF CNV Call | |
|---|---|---|
| | Relative Coverage > 2.0 | Relative Coverage ≤ 2.0 | |
| True genome copy # > 12 | TP | FP | Precision TP/ (TP + FP) |
| True genome copy # ≤ 12 | FN | TN | Negative Predictive Value FN/(FN + TN) |
| | Sensitivity TP/ (TP + FN) | Specificity TN/ (TN + FP) | |

Acceptance criteria are defined as follows: All datasets with purity ≥30% must show ≥95% sensitivity and ≥95% specificity. Failure criteria are defined as follows: A dataset with purity ≥25% shows sensitivity or specificity <95%. In the event that a sample fails, all should be repeated.

Limit of Detection: As with the SNV analysis, the 6 different purities of the Limit of Detection ("LoD") sample will be used to assess the limit of detection for copy number amplifications. The limit of detection will be the lowest tumor purity where that tumor purity and all greater tumor purities have sensitivity ≥95% and specificity ≥99%. Acceptance criteria are defined as follows: The limit of detection must be ≤25% tumor purity. Failure criteria defined as follows: The limit of detection is >25% tumor purity.

Repeatability: The single synthetic patient sample with 100% tumor purity (used in the SNV study) will be run ten times for repeatability. Acceptance criteria defined as follows: All datasets must show >99.99% concordance between the first and subsequent replication. Failure criteria defined as follows: Any pipeline run that shows <99.99% concordance between observed versus expected. In the event that any of the samples fail to meet the acceptance criteria, all should be repeated.

The following discussion represents additional considerations associated with the disclosed, inventive subject matter. It should be appreciated that the disclosed techniques can be considered a Monte Carlo system that leverages existing, real-world data to construct one or more empirically derived genomic variant probability distributions. The system is configurable to leverage these variant probability distributions to generate synthetic WGS for one or more patients including tumor WGS as well as matched normal WGS.

In some embodiments, the generated synthetic data provides a microscope into avenues of optimization of the genomic analysis computing ecosystem. The synthetic data has well-defined, possibly deterministic, structure, which can be used to analyze the performance of each computing element in the analysis ecosystem with respect to the element's roles or responsibilities. For example, once the synthetic data has been generated is can be passed through a standard work flow. The performance or accuracy at east step of the work flow can be measured with respect to specific types of synthetically generated variants. This approach gives researchers insight into how each step of the work flow can be optimized, especially at the algorithm level, with respect to types of expected variants that occur in actual data.

It should be appreciated that the inventive methods significantly improve the development of genomic analysis devices and bioinformatic pipelines. Indeed, the inventive methods have a direct technical effect. For example, generating a synthetic digital genomic dataset as described in the inventive subject matter enables genomic analysis devices to be validated, with confidence, on a known data set containing known variations. Without synthetic datasets of the inventive subject matter, analytic devices are not able to validate bioinformatic pipelines completely in silico. Rather, such devices would require input of sequencing data, derived from samples, with no control on accuracy or precision of the sequence data. Indeed, the inventive subject matter permits validation of bioinformatic pipelines free from the data biases and errors prone to genome and exome sequencing, and as such provide substantially improvements in the field of genomic analysis.

Further, generation of synthetic digital genomic datasets permits researchers to customize the number of variants, frequency of variants, and types of variants in the synthetic dataset. Such customization permits bioinformatic pipelines to be tested, stressed, and designed toward specific applications (e.g., identifying high frequency SNVs, SNPs, indels, etc; identifying low frequency variants, identifying a particular type of variant with heightened specificity, selectivity, accuracy, or with a lower limit of detection, etc). It should be appreciated that generating synthetic datasets of the inventive subject matter also permits computational devices to perform functions (described above) that were not previously possible.

Example 2—RNA-Seq Bioinformatics Validation

Methods of the inventive subject matter were used to test/validate the performance of a genomic analysis computing device (RNA bioinformatics pipeline) with respect to algorithm implementation in accurately calling variants in a patient's genome using RNA-Seq bioinformatics. Synthetic RNA datasets and DNA datasets were constructed as described above. Advantageously, it is contemplated such datasets can be used to support CLIA validation of the pipeline. Inputs included (1) variant calls from WGS tumor and normal datasets and (2) tumor RNA sequencing at a total depth of 140 million reads across two separate library preparations. However, it should be appreciated that the inventive subject matter contemplates various read depths (e.g., at least 10 million, 50 million, 100 million, 150 million, 200 million, 300 million reads, etc) across a various library preparations (e.g., a single library, more than two, more than five, more than ten, more than twenty, more than thirty, etc).

In this case, the reported variants include (1) presence of expressed somatic SNVs in RNA-Seq, (2) presence of expressed germline SNVs in RNA-Seq, (3) presence of expressed somatic indels in RNA-Seq, (4) presence of expressed germline indels in RNA-Seq, and (5) gene transcript levels. These outputs were evaluated on the synthetic datasets and a report was generated. The report gives the specificity, selectivity, accuracy, and level of detection for the variants, using a panel of 20 synthetic patients close to the limit of detection (25% tumor cellular purity). Of course, more (e.g., 30 or more) or less (e.g., 10 or less) synthetic patients can be used at greater (e.g., 30-40%, 40-50%, or even greater) or lower (e.g., 5-15%, 15-25%) cellular purity. Also, one of the synthetic patients was run through 10 times at 100% tumor purity to assess the reproducibility of the pipeline, and additionally at substantially lower purities (e.g., 10%, 15%, 20%, 25%, 30%, 35%, 40%, 45%, and 50%) to establish the lower limit of detection.

In the present example, the reference variant set for germline expressed SNVs included sites meeting all of the following conditions: (1) for the input experimental DNA contrast, the site was a predicted germline SNV (note this includes both true positives and false positives from that assessment); (2) there were 2 or more reads supporting the variant in the 100% tumor purity contrast; and (3) the site has not been filtered out, according to the criteria noted below. The experimental variant set included sites meeting all of the following conditions: (1) the site is a positive germline SNV in the input experimental DNA contrast (note this includes both true positives and false positives); (2) there were 2 or more RNA reads supporting the variant in the experimental data; and (3) the site has not been filtered out, according to the criteria noted below. For the 100% reference RNA dataset, sites with fewer than 20 total reads were filtered out. Further, sites in the reference RNA with only a single read supporting the variant were filtered out. It is contemplated such filtering excludes genes that are not constitutively expressed.

It is further contemplated that genome analysis algorithms can be modified to incorporate a variety of improved features. For example, in the present instance the genome analysis algorithms includes the following features: (1) an operation to call fusion genes from RNA-seq data; (2) an operation to determine expression of SNVs and indels (both germline and somatic) using "local" aligned RNA sequencing data and a de Brujin graph; (3) an operation to improve soft-clip consensus determinations to allow for multiple consensus sequences to co-exist at the same location in a transcriptome; and (4) allowing for more than one gene fusion candidate per pair of genes. It should be appreciated that modification of the genome analysis algorithms and validation by methods of the inventive subject matter demonstrate improved accuracy, specificity, and selectivity of the algorithms, including for example improved calling performance of EGFRvIII in simulated data.

In this example, for each of the described variant classes (expressed somatic SNV, expressed germline SNV, expressed somatic indel, expressed germline indel, and gene transcription level) the accuracy, limit of detection, and reproducibility of genome analysis algorithms was assessed. The accuracy of the algorithms was assessed across 20 synthetic patient samples. The limit of detection (for non-germline variants) of the algorithms was assessed using one sample from the 20 synthetic patient samples run at different tumor purities. The reproducibility of the results of the algorithms was assessed by running the sample from the LoD assessment through the algorithms an additional nine times at 100% purity.

A summary of the validation results is reported in Table 6. Unless stated otherwise, the pass criteria for PPV, sensitivity, specificity, and reproducibility with respect to each variant class are as described above. Advantageously, the method of the inventive subject matter revealed that the genome analysis algorithms passed the criteria for PPV, sensitivity, and specificity, as well as reproducibility and LoD for somatic variants and gene transcript levels.

TABLE 6

| Variant type | PPV/ Sens/Spec | Reproducibility | Limit of detection |
| --- | --- | --- | --- |
| Somatic SNV | Pass | Pass | Pass (20.0%) |
| Germline SNV | Pass | Pass | N/A |
| Somatic Indel | Pass | Pass | Pass (25.0%) |
| Germline Indel | Pass | Pass | N/A |
| Gene Transcript | Pass | Pass | Pass |

Assessment of Expressed Somatic SNVs

Expressed Somatic SNV Accuracy Across a Variety of Samples: The PPV, sensitivity, and specificity of the genome analysis algorithms for calling expressed somatic SNVs was assessed using 20 synthetic patients with 30% cellular purity, with detailed results presented in Table 7. Advantageously, the algorithms were validated by satisfying the passing criteria for every single synthetic patient (>=95% PPV, >=95% sensitivity, and >=99% specificity) with respect to calling expressed somatic SNVs.

TABLE 7

| TEST | TP | FP | FN | TN | SENS | SPEC | PPV |
| --- | --- | --- | --- | --- | --- | --- | --- |
| run23-var1-30 | 667 | 0 | 7 | 75454966 | 98.96142% | 100% | 100% |
| run23-var2-30 | 633 | 0 | 5 | 75455059 | 99.2163% | 100% | 100% |
| run23-var3-30 | 588 | 0 | 8 | 75455079 | 98.65772% | 100% | 100% |
| run23-var4-30 | 613 | 0 | 4 | 75455007 | 99.3517% | 100% | 100% |
| run23-var5-30 | 717 | 0 | 5 | 75454878 | 99.30748% | 100% | 100% |
| run23-var6-30 | 591 | 0 | 9 | 75455122 | 98.5% | 100% | 100% |
| run23-var7-30 | 534 | 0 | 5 | 75455221 | 99.07236% | 100% | 100% |
| run23-var8-30 | 619 | 0 | 6 | 75454950 | 99.04% | 100% | 100% |
| run23-var9-30 | 699 | 0 | 9 | 75454749 | 98.72881% | 100% | 100% |
| run23-var10-30 | 720 | 0 | 8 | 75454749 | 98.9011% | 100% | 100% |
| run23-var11-30 | 633 | 0 | 3 | 75454990 | 99.5283% | 100% | 100% |
| run23-var12-30 | 738 | 0 | 4 | 75454824 | 99.46092% | 100% | 100% |
| run23-var13-30 | 739 | 0 | 7 | 75454692 | 99.06166% | 100% | 100% |
| run23-var14-30 | 656 | 0 | 8 | 75454820 | 98.79518% | 100% | 100% |
| run23-var15-30 | 637 | 0 | 12 | 75454864 | 98.151% | 100% | 100% |

TABLE 7-continued

| TEST | TP | FP | FN | TN | SENS | SPEC | PPV |
|---|---|---|---|---|---|---|---|
| run23-var16-30 | 674 | 0 | 10 | 75455047 | 98.53801% | 100% | 100% |
| run23-var17-30 | 733 | 0 | 12 | 75454806 | 98.38926% | 100% | 100% |
| run23-var18-30 | 721 | 1 | 16 | 75454638 | 97.82904% | 100% | 99.8615% |
| run23-var19-30 | 701 | 0 | 9 | 75454791 | 98.73239% | 100% | 100% |
| run23-var20-30 | 709 | 0 | 8 | 75454765 | 98.88424% | 100% | 100% |

Expressed Somatic SNV Assay Repeatability: Repeatability of the results of the genome analysis algorithms for calling expressed somatic SNVs was assessed by running a single synthetic patient sample (variant 20) with 100% tumor purity ten times, with detailed results presented in Table 8. Advantageously, the algorithms were validated by satisfying the passing criteria for repeatability (>99.99% concordance between the first and subsequent replication) with respect to calling expressed somatic SNVs.

TABLE 8

| TEST | TP | FP | FN | TN | SENS | SPEC | PPV |
|---|---|---|---|---|---|---|---|
| run23-var20-100-2 | 738 | 0 | 0 | 75454763 | 100% | 100% | 100% |
| run23-var20-100-3 | 738 | 0 | 0 | 75454763 | 100% | 100% | 100% |
| run23-var20-100-4 | 738 | 0 | 0 | 75454763 | 100% | 100% | 100% |
| run23-var20-100-5 | 738 | 0 | 0 | 75454763 | 100% | 100% | 100% |
| run23-var20-100-6 | 738 | 0 | 0 | 75454763 | 100% | 100% | 100% |
| run23-var20-100-7 | 738 | 0 | 0 | 75454763 | 100% | 100% | 100% |
| run23-var20-100-8 | 738 | 0 | 0 | 75454763 | 100% | 100% | 100% |
| run23-var20-100-9 | 738 | 0 | 0 | 75454763 | 100% | 100% | 100% |
| run23-var20-100-10 | 738 | 0 | 0 | 75454763 | 100% | 100% | 100% |

Expressed Somatic SNV Limit of Detection: The LoD of the genome analysis algorithms for calling expressed somatic SNVs was assessed by running a single synthetic patient sample (variant 20) at 10%, 20%, 25%, 30%, 40%, and 50% tumor purity, with detailed results presented in Table 9. Advantageously, all samples passed the acceptance criteria (>=75% PPV, >=99% specificity, and >=95% sensitivity) with a 20% cell purity limit of detection with respect to calling expressed somatic SNVs.

TABLE 9

| TEST | Tumor % | TP | FP | FN | TN | SENS | SPEC | PPV |
|---|---|---|---|---|---|---|---|---|
| run23-var20-10 | 10 | 305 | 0 | 30 | 75454765 | 91.04478% | 100% | 100% |
| run23-var20-20 | 20 | 609 | 0 | 21 | 75454765 | 96.66667% | 100% | 100% |
| run23-var20-25 | 25 | 653 | 0 | 22 | 75454764 | 96.74074% | 100% | 100% |
| run23-var20-30 | 30 | 709 | 0 | 8 | 75454765 | 98.88424% | 100% | 100% |
| run23-var20-40 | 40 | 733 | 0 | 1 | 75454765 | 99.86376% | 100% | 100% |
| run23-var20-50 | 50 | 736 | 0 | 1 | 75454765 | 99.86431% | 100% | 100% |

Assessment of Expressed Germline SNVs

Expressed Germline SNV Accuracy Across a Variety of Samples: The PPV, sensitivity, and specificity of the genome analysis algorithms for calling expressed germline SNVs was assessed using 20 synthetic patients with 30% cellular purity, with detailed results presented in Table 10. Advantageously, the algorithms were validated by satisfying the passing criteria for every single synthetic patient (>=95% PPV, >=95% sensitivity, and >=99% specificity) with respect to calling expressed germline SNVs.

TABLE 10

| TEST | TP | FP | FN | TN | SENS | SPEC | PPV |
|---|---|---|---|---|---|---|---|
| run23-var1-30 | 14650 | 16 | 12 | 75390940 | 99.91816% | 99.99998% | 99.8909% |
| run23-var2-30 | 13943 | 21 | 4 | 75392727 | 99.97132% | 99.99997% | 99.84961% |
| run23-var3-30 | 13778 | 17 | 6 | 75392337 | 99.95647% | 99.99998% | 99.87677% |
| run23-var4-30 | 14305 | 21 | 7 | 75391264 | 99.95109% | 99.99997% | 99.85341% |
| run23-var5-30 | 14508 | 16 | 10 | 75391524 | 99.93112% | 99.99998% | 99.88984% |
| run23-var6-30 | 14760 | 18 | 8 | 75389908 | 99.94583% | 99.99998% | 99.8782% |
| run23-var7-30 | 13857 | 12 | 9 | 75391056 | 99.93509% | 99.99998% | 99.91348% |
| run23-var8-30 | 14522 | 5 | 8 | 75390489 | 99.94494% | 99.99999% | 99.96558% |
| run23-var9-30 | 14739 | 13 | 6 | 75389483 | 99.95931% | 99.99998% | 99.91188% |
| run23-var10-30 | 14298 | 21 | 4 | 75391434 | 99.97203% | 99.99997% | 99.85334% |
| run23-var11-30 | 14317 | 14 | 8 | 75391520 | 99.94415% | 99.99998% | 99.90231% |
| run23-var12-30 | 14564 | 21 | 11 | 75391637 | 99.92453% | 99.99997% | 99.85602% |
| run23-var13-30 | 14489 | 21 | 6 | 75391067 | 99.95861% | 99.99997% | 99.85527% |
| run23-var14-30 | 14318 | 20 | 9 | 75391389 | 99.93718% | 99.99997% | 99.86051% |
| run23-var15-30 | 14149 | 15 | 7 | 75391466 | 99.95055% | 99.99998% | 99.8941% |
| run23-var16-30 | 14783 | 14 | 3 | 75389841 | 99.97971% | 99.99998% | 99.90539% |
| run23-var17-30 | 14517 | 21 | 7 | 75391490 | 99.9518% | 99.99997% | 99.85555% |

TABLE 10-continued

| TEST | TP | FP | FN | TN | SENS | SPEC | PPV |
|---|---|---|---|---|---|---|---|
| run23-var18-30 | 14527 | 19 | 9 | 75390980 | 99.93808% | 99.99997% | 99.86938% |
| run23-var19-30 | 14693 | 14 | 8 | 75390509 | 99.94558% | 99.99998% | 99.90481% |
| run23-var20-30 | 15003 | 22 | 5 | 75390529 | 99.96668% | 99.99997% | 99.85358% |

Expressed Germline SNV Assay Repeatability: Repeatability of the results of the genome analysis algorithms for calling expressed germline SNVs was assessed by running a single synthetic patient sample (variant 20) with 100% tumor purity ten times, with detailed results presented in Table 11. Advantageously, the algorithms were validated by satisfying the passing criteria for repeatability (>99.99% concordance between the first and subsequent replication) with respect to calling expressed germline SNVs.

TABLE 11

| TEST | TP | FP | FN | TN | SENS | SPEC | PPV |
|---|---|---|---|---|---|---|---|
| run23-var20-100-2 | 15032 | 0 | 0 | 75390551 | 100% | 100% | 100% |
| run23-var20-100-3 | 15032 | 0 | 0 | 75390551 | 100% | 100% | 100% |
| run23-var20-100-4 | 15032 | 0 | 0 | 75390551 | 100% | 100% | 100% |
| run23-var20-100-5 | 15032 | 0 | 0 | 75390551 | 100% | 100% | 100% |
| run23-var20-100-6 | 15032 | 0 | 0 | 75390551 | 100% | 100% | 100% |
| run23-var20-100-7 | 15032 | 0 | 0 | 75390551 | 100% | 100% | 100% |
| run23-var20-100-8 | 15032 | 0 | 0 | 75390551 | 100% | 100% | 100% |
| run23-var20-100-9 | 15032 | 0 | 0 | 75390551 | 100% | 100% | 100% |
| run23-var20-100-10 | 15032 | 0 | 0 | 75390551 | 100% | 100% | 100% |

Assessment of Expressed Somatic Indels

Expressed Somatic Indel Accuracy Across a Variety of Samples: The PPV, sensitivity, and specificity of the genome analysis algorithms for calling expressed somatic indels was assessed using 20 synthetic patients with 30% cellular purity, with detailed results presented in Table 12. Advantageously, the algorithms were validated by satisfying the passing criteria for every single synthetic patient (>=95% PPV, >=95% sensitivity, and >=99% specificity) with respect to calling expressed somatic indels.

TABLE 12

| TEST | TP | FP | FN | TN | SENS | SPEC | PPV |
|---|---|---|---|---|---|---|---|
| run23-var1-30 | 247 | 0 | 5 | 75455700 | 98.01587% | 100% | 100% |
| run23-var2-30 | 218 | 0 | 2 | 75455720 | 99.09091% | 100% | 100% |
| run23-var3-30 | 216 | 0 | 1 | 75455721 | 99.53917% | 100% | 100% |
| run23-var4-30 | 232 | 0 | 3 | 75455717 | 98.7234% | 100% | 100% |
| run23-var5-30 | 253 | 0 | 3 | 75455723 | 98.82812% | 100% | 100% |
| run23-var6-30 | 249 | 0 | 4 | 75455676 | 98.41897% | 100% | 100% |
| run23-var7-30 | 218 | 0 | 4 | 75455679 | 98.1982% | 100% | 100% |
| run23-var8-30 | 198 | 0 | 6 | 75455733 | 97.05882% | 100% | 100% |
| run23-var9-30 | 247 | 0 | 5 | 75455671 | 98.01587% | 100% | 100% |

TABLE 12-continued

| TEST | TP | FP | FN | TN | SENS | SPEC | PPV |
|---|---|---|---|---|---|---|---|
| run23-var10-30 | 226 | 0 | 7 | 75455730 | 96.99571% | 100% | 100% |
| run23-var11-30 | 222 | 0 | 2 | 75455744 | 99.10714% | 100% | 100% |
| run23-var12-30 | 219 | 0 | 4 | 75455732 | 98.20628% | 100% | 100% |
| run23-var13-30 | 212 | 0 | 8 | 75455722 | 96.36364% | 100% | 100% |
| run23-var14-30 | 199 | 0 | 4 | 75455713 | 98.02956% | 100% | 100% |
| run23-var15-30 | 195 | 0 | 1 | 75455727 | 99.4898% | 100% | 100% |
| run23-var16-30 | 219 | 0 | 6 | 75455676 | 97.33333% | 100% | 100% |
| run23-var17-30 | 222 | 0 | 3 | 75455706 | 98.66667% | 100% | 100% |
| run23-var18-30 | 233 | 0 | 4 | 75455692 | 98.31224% | 100% | 100% |
| run23-var19-30 | 262 | 0 | 7 | 75455690 | 97.39777% | 100% | 100% |
| run23-var20-30 | 237 | 0 | 4 | 75455684 | 98.34025% | 100% | 100% |

Expressed Somatic Indel Assay Repeatability: Repeatability of the results of the genome analysis algorithms for calling expressed somatic indels was assessed by running a single synthetic patient sample (variant 20) with 100% tumor purity ten times, with detailed results presented in Table 13. Advantageously, the algorithms were validated by satisfying the passing criteria for repeatability (>99.99% concordance between the first and subsequent replication) with respect to calling expressed somatic indels.

TABLE 13

| TEST | TP | FP | FN | TN | SENS | SPEC | PPV |
|---|---|---|---|---|---|---|---|
| run23-var20-100-2 | 244 | 0 | 0 | 75455681 | 100% | 100% | 100% |
| run23-var20-100-3 | 244 | 0 | 0 | 75455681 | 100% | 100% | 100% |
| run23-var20-100-4 | 244 | 0 | 0 | 75455681 | 100% | 100% | 100% |
| run23-var20-100-5 | 244 | 0 | 0 | 75455681 | 100% | 100% | 100% |
| run23-var20-100-6 | 244 | 0 | 0 | 75455681 | 100% | 100% | 100% |
| run23-var20-100-7 | 244 | 0 | 0 | 75455681 | 100% | 100% | 100% |
| run23-var20-100-8 | 244 | 0 | 0 | 75455681 | 100% | 100% | 100% |
| run23-var20-100-9 | 244 | 0 | 0 | 75455681 | 100% | 100% | 100% |
| run23-var20-100-10 | 244 | 0 | 0 | 75455681 | 100% | 100% | 100% |

Expressed Somatic Indel Limit of Detection: The LoD of the genome analysis algorithms for calling expressed somatic indels was assessed by running a single synthetic patient sample (variant 20) at 10%, 20%, 25%, 30%, 40%, and 50% tumor purity, with detailed results presented in Table 14. Advantageously, all samples passed the acceptance criteria (>=75% PPV or >=99% specificity, and >=95% sensitivity) with a 25% cell purity limit of detection with respect to calling expressed somatic indels.

TABLE 14

| TEST | Tumor % | TP | FP | FN | TN | SENS | SPEC | PPV |
|---|---|---|---|---|---|---|---|---|
| run23-var20-10 | 10 | 112 | 0 | 13 | 75455685 | 89.6% | 100% | 100% |
| run23-var20-20 | 20 | 205 | 0 | 11 | 75455683 | 94.90741% | 100% | 100% |
| run23-var20-25 | 25 | 216 | 0 | 11 | 75455683 | 95.15419% | 100% | 100% |
| run23-var20-30 | 30 | 237 | 0 | 4 | 75455684 | 98.34025% | 100% | 100% |
| run23-var20-40 | 40 | 242 | 0 | 2 | 75455682 | 99.18033% | 100% | 100% |
| run23-var20-50 | 50 | 243 | 0 | 1 | 75455681 | 99.59016% | 100% | 100% |

Assessment of Expressed Germline Indels

Expressed Germline Indel Accuracy Across a Variety of Samples: The PPV, sensitivity, and specificity of the genome analysis algorithms for calling expressed germline indels was assessed using 20 synthetic patients with 30% cellular purity, with detailed results presented in Table 15. Advantageously, the algorithms were validated by satisfying the passing criteria for every single synthetic patient (>=95% PPV, >=95% sensitivity, and >=99% specificity) with respect to calling expressed germline indels.

TABLE 15

| TEST | TP | FP | FN | TN | SENS | SPEC | PPV |
|---|---|---|---|---|---|---|---|
| run23-var1-30 | 235 | 0 | 1 | 75451320 | 99.57627% | 100% | 100% |
| run23-var2-30 | 222 | 2 | 1 | 75451492 | 99.55157% | 100% | 99.10714% |
| run23-var3-30 | 214 | 1 | 1 | 75451398 | 99.53488% | 100% | 99.53488% |
| run23-var4-30 | 218 | 1 | 0 | 75451423 | 100% | 100% | 99.54338% |
| run23-var5-30 | 230 | 2 | 0 | 75451415 | 100% | 100% | 99.13793% |
| run23-var6-30 | 240 | 0 | 0 | 75451270 | 100% | 100% | 100% |
| run23-var7-30 | 201 | 1 | 1 | 75451298 | 99.50495% | 100% | 99.50495% |
| run23-var8-30 | 226 | 0 | 0 | 75451239 | 100% | 100% | 100% |
| run23-var9-30 | 236 | 2 | 0 | 75451189 | 100% | 100% | 99.15966% |
| run23-var10-30 | 212 | 1 | 0 | 75451403 | 100% | 100% | 99.53052% |
| run23-var11-30 | 229 | 1 | 0 | 75451376 | 100% | 100% | 99.56522% |
| run23-var12-30 | 231 | 1 | 0 | 75451406 | 100% | 100% | 99.56897% |
| run23-var13-30 | 243 | 0 | 0 | 75451290 | 100% | 100% | 100% |
| run23-var14-30 | 213 | 0 | 0 | 75451383 | 100% | 100% | 100% |
| run23-var15-30 | 227 | 1 | 0 | 75451406 | 100% | 100% | 99.5614% |
| run23-var16-30 | 236 | 2 | 0 | 75451224 | 100% | 100% | 99.15966% |
| run23-var17-30 | 221 | 0 | 0 | 75451436 | 100% | 100% | 100% |
| run23-var18-30 | 234 | 4 | 0 | 75451408 | 100% | 99.99999% | 98.31933% |
| run23-var19-30 | 236 | 0 | 0 | 75451411 | 100% | 100% | 100% |
| run23-var20-30 | 234 | 0 | 0 | 75451309 | 100% | 100% | 100% |

Expressed Germline Indel Assay Repeatability: Repeatability of the results of the genome analysis algorithms for calling expressed germline indels was assessed by running a single synthetic patient sample (variant 20) with 100% tumor purity ten times, with detailed results presented in Table 16. Advantageously, the algorithms were validated by satisfying the passing criteria for repeatability (>99.99% concordance between the first and subsequent replication) with respect to calling expressed germline indels.

TABLE 16

| TEST | TP | FP | FN | TN | SENS | SPEC | PPV |
|---|---|---|---|---|---|---|---|
| run23-var20-100-2 | 235 | 0 | 0 | 75451300 | 100% | 100% | 100% |
| run23-var20-100-3 | 235 | 0 | 0 | 75451300 | 100% | 100% | 100% |
| run23-var20-100-4 | 235 | 0 | 0 | 75451300 | 100% | 100% | 100% |
| run23-var20-100-5 | 235 | 0 | 0 | 75451300 | 100% | 100% | 100% |
| run23-var20-100-6 | 235 | 0 | 0 | 75451300 | 100% | 100% | 100% |
| run23-var20-100-7 | 235 | 0 | 0 | 75451300 | 100% | 100% | 100% |
| run23-var20-100-8 | 235 | 0 | 0 | 75451300 | 100% | 100% | 100% |
| run23-var20-100-9 | 235 | 0 | 0 | 75451300 | 100% | 100% | 100% |
| run23-var20-100-10 | 235 | 0 | 0 | 75451300 | 100% | 100% | 100% |

Assessment of Gene Transcription Level Accuracy

Gene Transcription Level Accuracy Across a Variety of Samples: Table 17

TABLE 17

| sample1 | sample2 | log_pearson_r |
|---|---|---|
| run23-var1-30 | theoretical-run23-var1-30 | 0.97453458602 |
| run23-var2-30 | theoretical-run23-var2-30 | 0.978849483426 |
| run23-var3-30 | theoretical-run23-var3-30 | 0.978825708189 |
| run23-var4-30 | theoretical-run23-var4-30 | 0.975831180094 |
| run23-var5-30 | theoretical-run23-var5-30 | 0.975807791114 |

TABLE 17-continued

| sample1 | sample2 | log_pearson_r |
|---|---|---|
| run23-var6-30 | theoretical-run23-var6-30 | 0.975272067351 |
| run23-var7-30 | theoretical-run23-var7-30 | 0.977772876591 |
| run23-var8-30 | theoretical-run23-var8-30 | 0.978249774176 |
| run23-var9-30 | theoretical-run23-var9-30 | 0.977839115068 |
| run23-var10-30 | theoretical-run23-var10-30 | 0.973390638596 |
| run23-var11-30 | theoretical-run23-var11-30 | 0.975794820664 |

TABLE 17-continued

| sample1 | sample2 | log_pearson_r |
|---|---|---|
| run23-var12-30 | theoretical-run23-var12-30 | 0.97510406599 |
| run23-var13-30 | theoretical-run23-var13-30 | 0.976313949808 |
| run23-var14-30 | theoretical-run23-var14-30 | 0.975456577828 |
| run23-var15-30 | theoretical-run23-var15-30 | 0.976355426612 |
| run23-var16-30 | theoretical-run23-var16-30 | 0.976021753081 |
| run23-var17-30 | theoretical-run23-var17-30 | 0.974696535669 |
| run23-var18-30 | theoretical-run23-var18-30 | 0.975601729431 |
| run23-var19-30 | theoretical-run23-var19-30 | 0.975387077531 |
| run23-var20-30 | theoretical-run23-var20-30 | 0.975053524191 |

Gene Transcription Level Accuracy Assay Repeatability: Results are presented in Table 18. All samples passed the acceptance criteria.

TABLE 18

| sample1 | sample2 | log_pearson_r |
|---|---|---|
| run23-var20-100_2 | theoretical-run23-var20-100-2 | 0.981581266214 |
| run23-var20-100_3 | theoretical-run23-var20-100-3 | 0.981581266214 |
| run23-var20-100_4 | theoretical-run23-var20-100-4 | 0.981581266214 |
| run23-var20-100_5 | theoretical-run23-var20-100-5 | 0.981581266214 |
| run23-var20-100_6 | theoretical-run23-var20-100-6 | 0.981581266214 |
| run23-var20-100_7 | theoretical-run23-var20-100-7 | 0.981581266214 |
| run23-var20-100_8 | theoretical-run23-var20-100-8 | 0.981581266214 |
| run23-var20-100_9 | theoretical-run23-var20-100-9 | 0.981581266214 |
| run23-var20-100_10 | theoretical-run23-var20-100-10 | 0.981581266214 |

Gene Transcription Level Accuracy Limit of Detection: Results are presented in Table 19. All samples passed the acceptance criteria. Note that this is the theoretical limit of detection between two completely uncorrelated expression profiles. Because these are not biologically realistic conditions, this assessment mostly tests the behavior of Pearson r, more than anything biologically relevant. It is contemplated that future tests to assess the level of over or under expression will more meaningfully assess a limit of detection.

TABLE 19

| sample1 | sample2 | LoD % | log_pearson_r |
|---|---|---|---|
| run23-var20-10 | theoretical-run23-var20-normal | 90 | 0.964731 |
| run23-var20-20 | theoretical-run23-var20-normal | 80 | 0.938718 |
| run23-var20-25 | theoretical-run23-var20-normal | 75 | 0.938683 |
| run23-var20-30 | theoretical-run23-var20-normal | 70 | 0.907474 |
| run23-var20-40 | theoretical-run23-var20-normal | 60 | 0.871301 |
| run23-var20-50 | theoretical-run23-var20-normal | 50 | 0.830213 |

Example 3—Select RNA Fusion Detection Validation

Methods of the inventive subject matter were used to test/validate the performance of a genomic analysis computing device (bioinformatics pipeline) with respect to algorithm implementation in accurately calling expressed fusion genes from RNA-seq data. Preferably, the input to the pipeline is an RNA-seq sample and a core set of fusion anchors. It is contemplated that the output of the pipeline includes a list of fusions, each fusion prediction consisting of the anchor gene, the fusion partner, and the level of support. Performance of the pipeline is evaluated on (1) synthetic fusion data, (2) on third party fusion standards in the form of cell pellets (lab standards), and (3) on clinical samples sequenced from formalin-fixed paraffin-embedded ("FFPE"). Reports are generated for the positive predictive value, the sensitivity, and the limit of detection of the analysis. Advantageously, it is contemplated such datasets and reports can be used to support CLIA validation of the pipeline.

As used herein, "gene fusion" refers to a sequence variant where an upstream portion and a downstream portion of two different human transcripts are expressed in a single transcript. It is contemplated that exceptions can be made to this definition, such as the case of EGFRvIII where both upstream and downstream transcript belong to EGFR (same human transcript) rather than two different human transcripts.

As used herein, "transcripts per million" ("TPM") refers to a measure of the frequency of a gene's transcripts or of the frequency of an individual transcript of a gene in a population of a million transcripts. Further, "log 2-TPM" refers to the base-2 logarithm of 1 plus the TPM: log 2(1+tpm). Such a calculation maps zero to zero and 1.0 to 1.0, and compresses the dynamic range logarithmically.

It is contemplated that synthetic whole genome sequencing specimens and exome specimens are constructed (or imported) used. Additionally, synthetic RNA-seq specimens will be generated according to this procedure.

Data Sets

Table 20 describes the samples used for the third party fusion standards analysis. It should be appreciated that additional or different samples with various cell purities (e.g., 20%, 30%, 40%, 60%, 70%, 80% 90%, 100%, etc) and/or various fusions (e.g., BCR-ABL1, AFF1-KMT2A, WWTR1-CAMTA1, EWSR1-FLI1, EWSR1-FLI-1, SS18-SSX2, BCAS4-BCAS3, NUP214-XKR3, RP2-BRAF, LMNA-NTRK1; see also FusionCancer database, accessible at www.donglab.ecnu.edu.cn/databases/FusionCancer/) can be used as appropriate.

TABLE 20

| Sample Name | Horizon Product | Purity | Fusion |
|---|---|---|---|
| 1 | HD-C134P | 50% | EML4-ALK |
| 3 | HD-C141P | 50% | SLC34A2-ROS1 |
| 4 | HD-D011 | | NTRK1-TPM3 |
| 5 | HD-D016 | | ETV6-NTRK3 |

Table 21 describes the samples used for the analysis of clinical samples sequenced from FFPE. It should be appreciated that additional or different fusions can also be used, as described above. The suffix '-nmx' is used to identify samples sequenced by one CLIA laboratory, possibly with an additional numeral to specify replicate number.

TABLE 21

| Fusion | Sample ID |
|---|---|
| ALK negative | CF0348-nmx |
| ROS1 negative | CF0348-nmx2 |
| KIAA1549-BRAF | CF0768-nmx |
| | CF0768-nmx2 |
| ALK negative | CF0848-nmx |
| ROS1 indefinite | CF0848-nmx2 |
| ALK negative | CF0902-nmx |
| ALK negative | CF1027-nmx |
| ROS1 negative | |
| FGFR2-EIF3A | 15-0-B1-nmx |
| | 15-1-B1-nmx |
| | 15-1-B2-nmx |
| | 15-2-B1-nmx |

Performance of the genome analysis algorithms will be assessed on three sets of samples: (1) Synthetic data (constructed fusion data with a known gold standard, and used to provide estimates of sensitivity, PPV, specificity, and limit of detection of gene fusion calling); (2) Lab standards (cell lines that contain a particular fusion (and possibly others), and used to assess sensitivity of gene fusion calling); and (3) Clinical samples (samples sequenced from FFPE to estimate precision of gene fusion calling on clinical samples).

Generation of Synthetic Data: RNA-seq from synthetic patients are generated on top of the synthetic DNA datasets and synthetic RNA datasets as described above. Random RNA fusion transcripts are created for 63 downstream fusion partners as described in Table 22.

TABLE 22

| | | | |
|---|---|---|---|
| AKT3 (NM_181690.2) | ETV5 (NM_004454.2) | MUSK (NM_005592.3) | PPARG (NM_138712.3) |
| ALK (NM_004304.4) | ETV6 (NM_001987.4) | MYB (NM_001130173.1) | PRKCA (NM_002737.2) |
| ARHGAP26 (NM_015071.4) | EWSR1 (NM_013986.3) | MYC (NM_002467.4) | PRKCB (NM_002738.6) |
| AXL (NM_021913.4) | FGFR1 (NM_023110.2) | NOTCH1 (NM_017617.3) | RAF1 (NM_002880.3) |
| BCL2 (NM_000633.2) | FGFR2 (NM_022970.3) | NOTCH2 (NM_024408.3) | RARA (NM_000964.3) |
| BCR (NM_004327.3) | FGFR3 (NM_000142.4) | NRG1 (NM_013962.2) | RELA (NM_021975.3) |
| BRAF (NM_004333.4) | FGR (NM_005248.2) | NTRK1 (NM_002529.3) | RET (NM_020975.4) |
| BRCA1 (NM_007294.3) | INSR (NM_000208.2) | NTRK2 (NM_006180.4) | ROS1 (NM_002944.2) |
| BRCA2 (NM_000059.3) | JAK2 (NM_004972.3) | NTRK3 (NM_001012338.2) | RSPO2 (NM_178565.4) |
| BRD3 (NM_007371.3) | KIT (NM_000222.2) | NUMBL (NM_004756.4) | RSPO3 (NM_032784.4) |
| BRD4 (NM_058243.2) | MAML2 (NM_032427.3) | NUTM1 (NM_001284292.1) | TERT (NM_198253.2) |

TABLE 22-continued

| | | | |
|---|---|---|---|
| EGFR (NM_005228.3) | MAST1 (NM_014975.2) | PDGFB (NM_002608.2) | TFE3 (NM_006521.5) |
| ERG (NM_001136154.1) | MAST2 (NM_015112.2) | PDGFRA (NM_006206.4) | TFEB (NM_007162.2) |
| ESR1 (NM_001122742.1) | MET (NM_001127500.1) | PDGFRB (NM_002609.3) | THADA (NM_001083953.1) |
| ETV1 (NM_001163148.1) | MSH2 (NM_000251.2) | PIK3CA (NM_006218.2) | TMPRSS2 (NM_005656.3) |
| ETV4 (NM_001986.2) | MSMB (NM_002443.3) | PKN1 (NM_213560.1) | |

An upstream fusion partner for each transcript is chosen at random from other canonical Ref-Seq transcripts without replacement. Any transcript that has undergone copy number modifications to any exons is excluded from selection. If both the paternal and maternal alleles of a gene in the tumor reference are without copy number modifications, then either the maternal or paternal allele is chosen at random. Given the upstream and downstream fusion partners, a boundary exon is chosen randomly from the upstream fusion partner. A downstream fusion exon is chosen randomly from the exons that have a compatible phase.

Fusion transcripts are created from these boundary exons either with or without interruption. Without interruption, genomic DNA is selected from the somatic reference genome, from the start of the 5' upstream exon up to and including the upstream boundary exon, and fused to the downstream boundary exon through to the 3' exon of the downstream gene. With interruption, the upstream or downstream exon is chosen randomly, then a random number of codons are deleted from that exon boundary. It is also contemplated that a transcript for the EGFRvIII exon skipping event can be created from one of the parent alleles at a TPM of 100.

It is contemplated that Fusion transcript levels are generated at the levels greater than 10, 20, 30, greater than 100 TPM, but preferably up to 100 TPM. Up to three fusion transcripts are generated at each level, with preferably at most two without interruption and at most 1 with interruption, at each level.

Assessment of Gene Fusion Detection

Gene fusions predictions are absence/presence predictions, and will be evaluated similarly to DNA variants.

Reportable Range of Fusion Products: The bioinformatics pipeline may potentially report a fusion product with one of the genes in Table 23 as an upstream or downstream partner. It is contemplated that these genes at least be evaluated using synthetic data. A prediction would include one of the seed genes in Table 23, either as the upstream or downstream gene, and another one of the other 25,464 RefSeq genes. It is also contemplated that EGFR can be tested for self-fusion for the EGFRvIII variant. It should be appreciated this results in a total of 1+2*74*25,464=3,768,673 possible predictions per sample.

TABLE 23

| | | | |
|---|---|---|---|
| AKT3 (NM_181690.2) | ETV1 (NM_001163148.1) | MSH2 (NM_000251.2) | PPARG (NM_138712.3) |
| ALK (NM_004304.4) | ETV4 (NM_001986.2) | MSMB (NM_002443.3) | PRKCA (NM_002737.2) |
| ARHGAP26 (NM_015071.4) | ETV5 (NM_004454.2) | MUSK (NM_005592.3) | PRKCB (NM_002738.6) |
| AXL (NM_021913.4) | ETV6 (NM_001987.4) | MYB (NM_001130173.1) | RAF1 (NM_002880.3) |
| BCL2 (NM_000633.2) | EWSR1 (NM_013986.3) | MYC (NM_002467.4) | RARA (NM_000964.3) |
| BCR (NM_004327.3) | FGFR1 (NM_023110.2) | NOTCH1 (NM_017617.3) | RELA (NM_021975.3) |
| BRAF (NM_004333.4) | FGFR2 (NM_022970.3) | NOTCH2 (NM_024408.3) | RET (NM_020975.4) |
| BRCA1 (NM_007294.3) | FGFR3 (NM_000142.4) | NRG1 (NM_013962.2) | ROS1 (NM_002944.2) |
| BRCA2 (NM_000059.3) | FGR (NM_005248.2) | NTRK1 (NM_002529.3) | RSPO2 (NM_178565.4) |
| BRD3 (NM_007371.3) | INSR (NM_000208.2) | NTRK2 (NM_006180.4) | RSPO3 (NM_032784.4) |
| BRD4 (NM_058243.2) | JAK2 (NM_004972.3) | NTRK3 (NM_001012338.2) | *TCF3 (NM_003200.3) |
| EGFR (NM_005228.3) | KIT (NM_000222.2) | NUMBL (NM_004756.4) | TERT (NM_198253.2) |
| ERG (NM_001136154.1) | MAML2 (NM_032427.3) | NUTM1 (NM_001284292.1) | TFE3 (NM_006521.5) |
| ESR1 (NM_001122742.1) | MAST1 (NM_014975.2) | PDGFB (NM_002608.2) | TFEB (NM_007162.2) |
| | MAST2 (NM_015112.2) | PDGFRA (NM_006206.4) | THADA (NM_001083953.1) |
| | MET (NM_001127500.1) | PDGFRB (NM_002609.3) | TMPRSS2 (NM_005656.3) |
| | | PIK3CA (NM_006218.2) | |
| | | PKN1 (NM_213560.1) | |

Experimental & Reference Variant Sets: As described previously, a gene fusion prediction is an ordered pairing of the upstream and downstream genes. Due to high homology, the upstream gene is referred to as a homology group. Preferably, the homology group is the set of all genes with >80% DNA sequence identity on the portion of the gene used in the fusion, but it can also include >75%, >70%, >65%, >60%, or >50% DNA sequence identity.

The reference variant set for gene fusions is the list of gene fusions that were spiked in with the all following conditions (selection criteria): (1) the fusion was functional (e.g., not a target of nonsense mediated decay); (2) the fusion was spiked in at a TPM of 20 or greater after multiplying by tumor purity (e.g., a TPM of 20 in a 100% pure sample corresponds to a TPM of 6 in a 30% sample); and (3) aside from EGFR-EGFR for the EGFRvIII variant, fusion is not an internal gene fusion.

The experimental variant set will be those sites for which all of the following hold: (1) the site is labeled as a PASS call in the VCF; (2) the site has a minimum read support of 8 (the standard for fusion calling in the pipeline); and (3) the site is not labeled DENOVO in the VCF (e.g., not from an experimental fusion method).

Due to the difficulty of distinguishing between homologous genes as part of the fusion, the true possible prediction space is less than all possible genes, namely 19270*19269. However, it is also greater than 66*65, the list of potential fusions used in this test. While it is contemplated that a range from 19270*19269 to 66*65 be used as potential fusions, in preferred embodiments 66*65 is used as the more conservative estimate of specificity for predictions.

Accuracy Study: Accuracy will be assessed across a panel of synthetic patients. The reference data will be the synthetic gene fusions in RNA of 20 synthetic patients constructed using the teachings above and meeting the selection criteria above. The experimental data is the predicted fusions from the 100% RNA sample on all 20 synthetic patients. PPV, Sensitivity, and Specificity must be greater than 95% in all validation samples.

Reproducibility Study: Reproducibility is assessed using nine replicates of a single run. RNA FASTQ data from the 100% purity limit of detection sample is the reference data. It will be processed through the RNA bioinformatics pipeline. The same FASTQ data that was used as the reference is processed an additional nine times. To meet acceptance criteria, all reproducibility runs must show >=99.99% accuracy and concordance with the previous run. Any experimental run with <99.99% accuracy or concordance with the previous run is a failing run.

Limit of Detection Study: LoD is assessed as the minimum TPM level at which genes fusion products are detectable. This is a function both of tumor purity and the TPM expression level in the synthetic tumor part. The reference sample data is the RNA FASTQ data from the 100% sample. The experimental data is the RNA FASTQ samples at 30% and 100% tumor purities. It should be appreciated that various other tumor purities can be used as appropriate (e.g., 15%, 20%, 25%, 35%, 40%, etc). Sensitivity of the predictor will be measured by binning the true fusions into bins of 0-20 TPM, 20-50 TPM, 50-100 TPM, and 100+TPM. The LoD will be the lowest bin (by TPM) such that sensitivity is >95%. Preferably, the LoD is >20 TPM, though it is contemplated the LoD can be 15, 10, or less TPM. Thus, in preferred embodiments, if the limit of detection is <20 TPM then it has failed validation.

Assessment of Lab Standard Fusion Detection

The lab standards in Table 20 are used to assess sensitivity of fusion detection. For each sample, there will be a single variant, as specified in the Table 20 (reference variant set). RNA is extracted from cell pellets, and standard RNA-seq is performed to generate RNA FASTQ. In preferred embodiments, the RNA bioinformatics pipeline described above is run on the RNA FASTQ, though it should be appreciated that additional or different genomic analysis computing devices or genome analysis algorithms can also be used as appropriate.

The results from each sample run will be assessed as correct or incorrect for predicting the expected fusion in that sample. To satisfy the acceptance criteria, all runs on each sample must correctly predict the expected fusion, though it should be appreciated that in some cases a single or sum total of runs predicting the expected fusion can be deemed sufficient. In preferred embodiments, if any sample is incorrect, then the entire assessment fails.

Assessment of Clinical Samples

The clinical samples in Table 21 are used to assess PPV and limit of detection in the FFPE samples. For each sample, the single member of the reference set is the gene fusion listed in the first column of Table 21. In preferred embodiments, each fusion has been validated via an external CLIA laboratory. The experimental set of fusion calls will be all those that pass the filtering of the pipeline (e.g., genomic analysis computing device) that is being tested/validated.

Accuracy: Due to the limited number of samples available, all predictions made by the pipeline must be correct for each sample. Accuracy of the samples from the 7 patients identified in Table 21 are assessed.

Repeatability: To assess intermediate precision (repeatability), replicate samples are used. For example, CF0767-nmx2 and CF0848-nmx2 are replicate samples, produced from the same FFPE block as the original sample. In contrast, the ITOMICS 15 patient (15-0-B1-nmx, 15-1-B1-nmx, 15-1-B2-nmx, and 15-2-B1-nmx) has samples from four different tumors, and although the fusion is present in all four samples they cannot be considered replicates for diagnostic purposes. To confirm intermediate precision, all predictions must be correct, and preferably concordant between the replicate samples.

Limit of Detection: For a general limit of detection for RNAs, original RNA data from 15-1-B1 and B2 and CF0768-nmx and nmx2 will be subsetted down to 50%, 25%, 15%, and 10% of the original RNA amount, in triplicate. This has the effect of reducing the purity of the tumor to that amount, with the conservative estimate that the original tumor was 100% pure. For each fusion in the diluted sample, the TPM for the fusion is estimated for the LoD experiment. For example, in preferred embodiments the estimated fusion TPM of the 100% sample is the maximum TPM of the two constitutive genes, as estimated by RSEM. Advantageously, this does not account for non-fusion transcripts from these two genes; accounting for non-fusion transcripts would decrease the true TPM of the fusion product. By overestimating the TPM of the transcript, we establish a more conservative estimate of the LoD.

Example 4—SNV and Indel Detection in WES from Normal/FFPE Samples Validation

Methods of the inventive subject matter were used to test/validate the performance of a genomic analysis computing device (bioinformatics pipeline) with respect to algorithm implementation in accurately calling variants in FFPE exome sequencing data. The bioinformatics pipeline reports on both germline and somatic variants starting from unaligned reads from sequencing machines. Synthetic genomic datasets are constructed (e.g., by the methods described herein) and used to demonstrate both the limit of detection and repeatability of SNV and indel variant calls by the pipeline. Advantageously, it is contemplated such datasets and/or resulting reports can be used to support CLIA validation of the pipeline.

The pipeline inputs include (1) germline (blood) whole exome sequencing at a depth of 75× coverage and (2) tumor whole exome sequencing at a depth of 150× coverage. In preferred embodiments, accuracy of variant calling is increased by using all input data simultaneously in the statistical models to call variants, and preventing independent evaluation of the variants from each input. The reported variants include (1) germline SNVs, (2) germline indels, (3) somatic SNVs, and (4) somatic indels. These inputs are evaluated on a variety of clinical samples. In preferred embodiments, clinical sample data is used from at least two different CLIA laboratories. Advantageously, LoD is determined by a synthetic dilution of the cancer cell lines.

Table 24 identifies and describes the specimens used for clinical samples. Samples from these specimens may have a suffix denoting more information. The suffix '-nmx' is used to identify samples sequenced by one CLIA laboratory, possibly with an additional numeral to specify replicate number. The suffix '-rdx' specifies a sample sequenced by another CLIA laboratory, different than -nmx. The suffixes '-50' and '-250' refer to input DNA quantities of 50 ng and 250 ng.

TABLE 24

| Contrast name | Description |
| --- | --- |
| 05221956MD-A | clinical sample: external reproducibility |
| 15-19748-1-1 | clinical sample: external reproducibility |
| 191551407-SP07-1702 | clinical sample: external reproducibility |

TABLE 24-continued

| Contrast name | Description |
| --- | --- |
| 196086105 | clinical sample: intermediate precision, input quantity |
| CE0844 | clinical sample: external reproducibility |
| CF0424 | clinical sample: intermediate precision, input quantity |
| CF0528 | clinical sample: intermediate precision, input quantity |
| S15-21562 | clinical sample: external reproducibility |
| S15-26214 | clinical sample: external reproducibility |
| S15-28835 | clinical sample: external reproducibility, intermediate precision, input quantity |
| S15-373 | clinical sample: external reproducibility |
| S15-53735 | clinical sample: external reproducibility |
| SD12-4107 | clinical sample: external reproducibility |
| ST14-29 | clinical sample: external reproducibility, input quantity |
| colo829-lod-sc-10-exome | mix of lines COLO829 (10%) and COLO829BL (90%) |
| colo829-lod-sc-15-exome | mix of lines COLO829 (15%) and COLO829BL (85%) |
| colo829-lod-sc-25-exome | mix of lines COLO829 (25%) and COLO829BL (75%) |
| colo829-lod-sc-50-exome | mix of lines COLO829 (50%) and COLO829BL (50%) |

Sample Preparation: For COLO829 and COLO829BL, cell lines were cultured using culture conditions recommended by the supplier. Sample preparation was performed and FFPE blocks and sections were generated by a CLIA laboratory. Genomic DNA was isolated from FFPE sections and exome DNA was enriched by the CLIA laboratory. The DNA from the blood sample was sequenced to an exome coverage depth of at least 75×, and the tumor sample was sequenced to an exome coverage of at least 150×. Preferably, FFPE tumor and blood is also processed by an independent CLIA laboratory for comparison (e.g., ResearchDX, LLC). Limit of detection samples were generated using a computational mixing approach, preferably one that has been validated for equivalence to molecular mixing. Multiple DNA libraries from the FFPE tumor and FFPE bloodline cell line COLO829 and COLO829BL were sequenced to allow mixture at various depths.

In preferred embodiments, four different validation studies are conducted, though it should be appreciated that in some cases it may be advantageous to conduct a single study, a partial combination of the described studies, or combination with some or all of the described studies with additional studies.

Validation Study 1: Comparison with external CLIA laboratory. For this study, results from a bioinformatic pipeline based on sequence data from one CLIA-licensed laboratory (first CLIA laboratory) are compared with results based on sequence data generated from an additional CLIA-licensed laboratory (e.g., ResearchDX) across at least one pair of samples. In preferred embodiments, 2, 3, 5, 10, 15, or more pairs of samples can be compared. The SNV calls generated from the exome data from the additional CLIA laboratory are used to generate reference calls. Data from the first CLIA laboratory are used as the experimental set. Preferably, to satisfy acceptance criteria and validate the bioinformatic pipeline, all datasets must show >=95% PPV, >=95% sensitivity, and >=99% specificity. In some embodiments, somatic tumor variants and germline variants are evaluated separately, as are indels and SNVs, for a total of four types of variants, though it should be appreciated in some instances not all variants are evaluated.

Validation Study 2: Reproducibility (Intermediate Precision). In this study, the reproducibility of a bioinformatic pipeline are evaluated for consistency of quality and results. Preferably, this is accomplished by comparing results from 2 replicates of 3 clinical samples for whole exome sequencing. However, it should be appreciated that more than 3, at least 5, or at least 10 samples may be used, and results from at least 3, at least 5, or at least 10 replicates may be compared. Further, replicates may be analyzed on different days, including 1, 2, 3, 4, 5, or 10 days apart. Advantageously, using at least 3 replicates of at least 3 samples increases the validity of bioinformatic pipeline when assessing reproducibility. In preferred embodiments, each pair of samples is compared in two ways: once with sample A as the gold standard, and once with sample B as the gold standard. To satisfy acceptance criteria, each such comparison must show >=95% PPV, >=95% sensitivity, and 99% specificity, when pooled across the comparisons. In some embodiments, somatic tumor variants and germline variants are evaluated separately, as are indels and SNVs, for a total of four types of variants, though it should be appreciated in some instances not all variants are evaluated.

Validation Study 3: Limit of Detection. Varying ratios of tumor and normal sequencing data from a pair of cell lines are generated and the impact of these differing proportions of cells are assessed. For example, a mixture of tumor purities for COLO829 can be prepared as described in Table 24. In preferred embodiments, the 100% sample is used as the gold standard set of variants. The limit of detection is evaluated as the lowest sample purity with >=95% sensitivity and >=99% specificity. Preferably, the LoD for a bioinformatic pipeline must be >=30% to validate the pipeline. In some embodiments, somatic tumor variants and germline variants are evaluated separately, as are indels and SNVs, for a total of four types of variants, though it should be appreciated in some instances not all variants are evaluated.

Validation Study 4: Input quantity. Bioinformatic pipeline results from two different quantities of input DNA will be compared (e.g., two different quantities selected from 10 ng, 20 ng, 30 ng, 40 ng, 50 ng, 75 ng, 100 ng, 150 ng, 200 ng, and 250 ng). In one preferred embodiment, various replicates that use a quantity of 50 ng will be used as the test data, while the gold standard will be replicates that use 250 ng of DNA as input. Preferably each pair of samples will be compared in two ways: once with sample A as the gold standard, and once with sample B as the gold standard. To satisfy acceptance criteria, each such comparison must show >=95% PPV, >=95% sensitivity, and 99% specificity, when pooled across the comparisons. In some embodiments, somatic tumor variants and germline variants are evaluated separately, as are indels and SNVs, for a total of four types of variants, though it should be appreciated in some instances not all variants are evaluated.

Additional Studies: In some cases, it may be advantageous to conduct different or additional studies. For example, a study may be conducted to evaluate low level DNA input. Such a study could advantageously demonstrate a bioinformatic pipeline unexpectedly returns acceptable results with lower than industry standard or recommended levels of DNA input. Further, it could be advantageous to evaluate the performance of a bioinformatic pipeline using a truth set (e.g., COLO829 consensus variant list) rather than taking gold standards from inferior quality data. Such studies may further satisfy clinical regulations by validating a bioinformatic pipeline with well characterized references. It should be appreciated that the methods and datasets of the inventive subject matter advantageously and unexpectedly allow for continuous validation of bioinformatic pipelines, including adapting to meet heightened or new validation thresholds as required by one or more regulatory agencies or industry standards.

Metrics and Performance Evaluation

It is contemplated that gold standard variants are identified in the reference data for each comparison by selecting a subset of calls from clonal variants in the cell line. For example, each coding base in the hg19 reference genome is classified according to the following status in the gold standard VCF: (1) mappable variant; (2) unmappable variant; and (3) reference site.

In some embodiments, mappable variants have VCF showing (1) a variant with >45% allele fraction after correction for sample impurity, (2) the site in the tumor BAM has a read depth of at least 20 reads with mapping quality greater than 10; (3) the site in the normal BAM has a read depth of at least 10 reads with mapping quality greater than 5; and (4) the variant in the gold sample receives a quality score of greater than 15. Thus, unmappable variant VCFs generally do not meet the criteria for a mappable variant. Preferably, reference sites are generally where the patient's synthetic genome is reference at that site.

Advantageously, in some cases a low variant allele frequency filter on FP calls can be used. If the 95% credibility interval (Jeffrey's binomial interval) of test variant allele frequency overlaps the 95% credibility interval of the gold variant allele frequency, then the FP will be excluded from the analysis as there is not sufficient power to assess the false positive as truly false positive.

Preferably, where output from a bioinformatic pipeline produces true negatives, metrics will include accuracy, sensitivity, and specificity as discussed above. Further, it should be appreciated that for gold germline variants, any call from the gold sample that passes standard filtering in the VCF can be used. As for SNV and indel predictions, the evaluated region is preferably the exonic regions of RefSeq genes, while for amplifications the entire genome is used as the evaluated region.

It should be appreciated that somatic indels are a relatively rare event in some cancer samples, making assessment of these events more challenging. In order to estimate the accuracy of the pipeline and sequencing data with greater confidence, advantageously special contrasts can be used that intentionally mismatch the normal sample. For example, there are typically far more uncommon germline coding indels than there are somatic indels in a tumor. By swapping the normal sample in the contrast, the majority of these germline indels now appear to be somatic, while advantageously still providing the opportunity to make variant calls on realistic data.

Example 5—SNV and Indel Detection in Synthetic Exome Data Validation

Methods of the inventive subject matter were used to test/validate the performance of a genomic analysis computing device (bioinformatics pipeline) with respect to algorithm implementation in accurately calling variants in a patient's exome. Synthetic genomic datasets were constructed, for example, by the methods described herein. Advantageously, it is contemplated such datasets can be used to support CLIA validation of the pipeline. Inputs to the pipeline included (1) Germline (blood) whole exome sequencing at a depth of 75× coverage and (2) Tumor whole exome sequencing at a depth of 150× coverage. In some cases, it is contemplated that sequencing the whole exome of both germline and tumor samples may improve results of the genome analysis algorithms.

All input data is used simultaneously in the statistical models to call variants, and the variants from each input cannot be evaluated independently. It is contemplated that such an approach increases the accuracy of variant calling. The reported variants (outputs) include (1) germline small nucleotide variants, (2) germline insertions and deletions, (3) somatic small nucleotide variants, and (4) somatic insertions and deletions. It is contemplated that these outputs are evaluated on synthetic data via methods of the inventive subject matter with every change/modification of the genome analysis algorithms, and a report will be generated to validate the algorithms. This report will give the accuracy and level of detection for these variants, using a panel of 20 synthetic patients close to the limit of detection (30% tumor cellular purity). Also, one of these patients will be run through 10 times at 100% tumor purity to assess the reproducibility of the pipeline, and additionally at 10%, 20, 25%, 30%, 40%, and 50% to establish the lower limit of detection.

Synthetic genomes for 20 patients were constructed according to the teachings previously described. During the genome and read generation process, all variants used were stored to be used as part of the gold standard during accuracy analysis. Exome read data were generated by sampling random locations within the exome enrichment kit design. While most exome enrichment kits (e.g. Agilent, etc.) are deemed appropriate, in preferred embodiments IDT (Integrated DNA Technologies) enrichment kits are used. However, it should be appreciated that differences in capture regions and capture efficiencies between exome enrichment kits can be controlled via depth filters. For example, use of coverage depths at 75× for the normal genome and 150× for the tumor genome, after correcting for 10% fragment duplicate rate, are contemplated. The following samples were generated: (1) limit of detection samples from the same simulated patient, at various tumor purities, and (2) variability samples, at 30% and 100% purity. It is contemplated that the 100% sample is used for determining mappability of synthetic variants.

Assessment of Somatic SNV Accuracy

SNV PPV, Sensitivity, and Specificity Across Many Samples: To assess the accuracy of a variety of patients at the limit of detection, it is contemplated that somatic variants of 20 synthetic patients (constructed as described above) are assayed at 30% tumor cellular purity.

Accuracy is defined as $(TP+TN)/(TP+TN+FP+FN)$; Positive predictive value (PPV) is defined as $TP/(TP+FP)$; Sensitivity is defined as $TP/(TP+FN)$; and Specificity is defined as $TN/(TN+FP)$. In preferred aspects, acceptance criteria are typically defined as follows: All datasets must show >=95% PPV, >=95% sensitivity, >=99% specificity, and >99% accuracy. In the event that any of the samples fail to meet the acceptance criteria, all should be repeated.

With respect to repeatability it is contemplated that a single synthetic patient sample with 100% tumor purity will be run ten times for repeatability. For this comparison, the initial run will be used as the gold standard for each reproducibility test. Here, acceptance criteria are typically defined as follows: All datasets must show >99.99% concordance between the first and subsequent replication, and failure criteria are typically defined as follows: Any subsequent run that shows <99.99% concordance between observed versus expected. As before, in the event that any of the samples fail to meet the acceptance criteria, all should be repeated.

Limit of Detection: The limit of detection for somatic SNVs will be assessed using the repeatability sample via a synthetic dilution. The percentage of tumor reads will typically be run at the following levels: 5%, 10% 15%, 20%, 25%, 30%, 40%, and 50%. The limit of detection will be the lowest purity dilution such that sensitivity is >=95%. The genome analysis algorithms will be validated (acceptance criteria) if the LoD is >=30%, and will be rejected (failure criteria) if the LoD is <30%.

Assessment of Germline SNV Detection

Germline accuracy across many samples: To assess the accuracy of germline variant calling, genotypes of the 20 different synthetic patients used in the SNV study will be assessed using the 30% tumor sample with matched normal data. In preferred aspects, acceptance criteria are defined as follows: All datasets must show >=95% PPV, >=95% sensitivity and >=99% specificity. Failure Criteria are defined as follows: Any dataset that shows <95% PPV, <95% sensitivity, or <99% specificity. In the event that any of the samples fail to meet the acceptance criteria, all should be repeated.

With respect to repeatability it is contemplated that the single synthetic patient sample with 100% tumor purity will be run ten times for repeatability. Acceptance criteria are defined as follows: All datasets must show >99.99% concordance between the first and subsequent replication. Failure criteria are defined as follows: Any run that shows <99.99% concordance between observed versus expected. In the event that any of the samples would fail to meet the acceptance criteria, all should be repeated.

Germline Limit of Detection: Since the allele fraction of germline variants does not change with tumor purity, the limit of detection was not assessed.

Assessment of Somatic Indels

Indel Sensitivity, and Specificity Across Many Samples: To assess the accuracy of a variety of patients at the limit of detection, somatic variants of 20 different synthetic patients were assayed at 30% tumor cellular purity. Accuracy will be assessed across the variability samples. Acceptance Criteria are defined as: The pooled results must show >=95% PPV, >=95% sensitivity and >=99% specificity. Failure criteria are defined as: Any dataset that shows <95% PPV, <95% sensitivity or <99% specificity.

Repeatability: A single synthetic patient sample with 100% tumor purity (e.g., sample used in the accuracy study) will be run ten times for repeatability. Acceptance Criteria are all datasets must show >99.99% concordance between the first and subsequent replication. Failure Criteria are any pipeline run that shows <99.99% concordance between observed versus expected. In the event that any of the samples fail to meet the acceptance criteria, all should be repeated.

Indel Limit of Detection: The limit of detection for somatic SNVs will be assessed with a synthetic dilution (e.g., 5%, 10% 15%, 20%, 25%, 30%, 40%, and 50% cell purity). The limit of detection will be the lowest purity dilution such that sensitivity is >=95%. The genome analysis algorithms will be validated (acceptance criteria) if the LoD is >=30%, and will be rejected (failure criteria) if the LoD is <30%.

Germline Indel Detection

Germline Accuracy Across Many Samples: To assess the accuracy of germline variant calling, genotypes of the 20 different synthetic patients used in the indel study will be assessed using the 30% tumor sample with matched normal data. In preferred aspects, acceptance criteria are defined as follows: All datasets must show >=95% PPV, >=95% sensitivity and >=99% specificity. Failure Criteria are defined as follows: Any dataset that shows <95% PPV, <95% sensitivity, or <99% specificity. In the event that any of the samples fail to meet the acceptance criteria, all should be repeated.

With respect to repeatability it is contemplated that the single synthetic patient sample with 100% tumor purity will be run ten times for repeatability. Acceptance criteria are defined as follows: All datasets must show >99.99% concordance between the first and subsequent replication. Failure criteria are defined as follows: Any run that shows <99.99% concordance between observed versus expected. In the event that any of the samples would fail to meet the acceptance criteria, all should be repeated.

Germline Limit of Detection: Since the allele fraction of germline variants does not change with tumor purity, the limit of detection was not assessed.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

What is claimed is:

1. A computer-implemented method of testing or validating an algorithm associated with genomic analysis, comprising:

introducing at least 500 single nucleotide polymorphism (SNP) sequences at a predetermined frequency and distribution into at least one set of autosome sequence data and a set of X-chromosome sequence data from a reference genome sequence to prepare a set of synthetic maternal autosome and X-Chromosome genome sequence data;

introducing at least 500 SNP sequences at a predetermined frequency and distribution into at least one set of autosome sequence data of the reference genome sequence and a set of X- or Y-chromosome sequence data of the reference genome sequence to prepare a set of synthetic paternal genome sequence data; and merging the maternal and paternal synthetic genome sequences data into a combined synthetic genomic dataset;

inputting the combined synthetic genomic dataset into the algorithm; and preparing a performance report listing deviations from the combined synthetic genomic dataset and wherein the maternal and paternal genome sequence data and synthetic genomic dataset are being manipulated on a non-transitory computer readable storage medium.

2. The method of claim 1 further comprising a step of sampling the combined synthetic genomic dataset to thereby produce a plurality of simulated reads.

3. The method of claim 2 wherein the step of sampling is performed to simulate a read coverage of at least 25×.

4. The method of claim 2 wherein the step of sampling is performed using a read error and base quality profile representative of a frozen tissue sample.

5. The method of claim 2 wherein the step of sampling is performed to produce simulated reads having a length of between 100 and 400 bases.

6. The method of claim 1 further comprising a step of including into the combined synthetic genomic dataset a list identifying type and position of the SNPs relative to the reference genome sequence data.

7. The method claim 1 further comprising a step of introducing into at least one of the synthetic maternal genome sequence data and the paternal genome sequence data a further genomic change selected from the group consisting of a single nucleotide variant (SNV), an indel, and a copy number alteration to thereby produce a synthetic somatic data set.

8. The method of claim 7 wherein the synthetic somatic data set further comprises a list identifying type and position of the further genomic change relative to the at least one of the synthetic maternal and paternal genome.

9. The method of claim 7 wherein the synthetic somatic data set further comprises a plurality of simulated reads from the synthetic somatic data set.

10. The method of claim 7 wherein the SNVs are based on at least one of COSMIC mutations, somatic TCGA mutations, and random locations in the genome.

11. The method of claim 7 wherein the copy number alteration is selected from the group consisting of (i) 25 small deletions, each with a size of 5,000 bp to 500,000 bp; (ii) 25 small tandem amplifications, each with a size of 5,000 bp to 500,000 bp and each having a copy number between 2 and 5; (iii) 10 small tandem hyperamplifications, with a size of 5,000 to 500,000 bp, and a copy number between 15 and 30; and (iv) large arm/chromosome deletions, each with a size between 30% and 100% of a chromosome, anchored to a telomere.

12. The method of claim 1 further comprising a step of including into the combined synthetic genomic dataset a plurality of simulated reads from the combined synthetic genomic dataset.

13. The method of claim 1, wherein the algorithm is an algorithm that groups a plurality of simulated reads from the combined synthetic genomic dataset.

14. The method of claim 1, wherein the algorithm is an algorithm that annotates a plurality or group of simulated reads from the combined synthetic genomic dataset.

15. The method of claim 1, wherein the algorithm is an algorithm that outputs a plurality of simulated reads from the combined synthetic genomic dataset between a sequencing device and an analysis engine.

16. The method of claim 1, wherein the algorithm is an algorithm that assembles and indexes a plurality of simulated reads from the combined synthetic genomic dataset.

17. The method of claim 1, wherein the algorithm is a variant calling algorithm.

18. A method of validating operation of a plurality of computing devices that are informationally coupled to each other, comprising a step of using the combined synthetic genomic dataset of claim 1 as an input into a first of the devices, and using an output of the first of the devices as input into a second of the devices.

* * * * *